(12) United States Patent
Bhatia et al.

(10) Patent No.: US 8,237,573 B2
(45) Date of Patent: Aug. 7, 2012

(54) ALARM UNIT FOR MONITORING OR DETECTION OF AN ANALYTE

(76) Inventors: Saket S. Bhatia, Santa Clara, CA (US);
Darrell E. Davis, Sunrise, FL (US);
Ankush S. Bhatia, Mumbai (IN)

( * ) Notice: Subject to any disclaimer, the term of this patent is extended or adjusted under 35 U.S.C. 154(b) by 94 days.

(21) Appl. No.: 12/946,851

(22) Filed: Nov. 15, 2010

(65) Prior Publication Data

US 2011/0234412 A1     Sep. 29, 2011

Related U.S. Application Data

(63) Continuation-in-part of application No. 12/661,823, filed on Mar. 25, 2010.

(51) Int. Cl.
*G08B 23/00* (2006.01)
(52) U.S. Cl. .................. 340/573.5; 340/573.1; 340/540
(58) Field of Classification Search ................ 340/573.5
See application file for complete search history.

(56) References Cited

U.S. PATENT DOCUMENTS

| | | | |
|---|---|---|---|
| 4,518,833 A | 5/1985 | Watkins | |
| 4,851,816 A | 7/1989 | Macias | |
| 5,036,859 A | 8/1991 | Brown | |
| 5,202,261 A | 4/1993 | Musho | |
| 5,220,919 A * | 6/1993 | Phillips et al. | 600/345 |
| 5,459,452 A | 10/1995 | DePonte | |
| 5,667,615 A | 9/1997 | Maurer | |
| 2004/0207530 A1 * | 10/2004 | Nielsen | 340/604 |
| 2005/0001728 A1 * | 1/2005 | Appelt et al. | 340/573.1 |
| 2006/0044143 A1 * | 3/2006 | Randolph | 340/573.5 |
| 2008/0041792 A1 | 2/2008 | Crnkovich | |
| 2008/0058745 A1 | 3/2008 | Long et al. | |
| 2008/0246620 A1 | 10/2008 | Page | |

FOREIGN PATENT DOCUMENTS

| | | |
|---|---|---|
| KR | 19960003514 B1 | 3/1996 |
| KR | 20010097963 A | 11/2001 |
| WO | PCT/JP2006/313995 | 1/2008 |
| WO | PCT/NZ2008/000331 | 6/2009 |

* cited by examiner

*Primary Examiner* — George Bugg
*Assistant Examiner* — Kerri McNally
(74) *Attorney, Agent, or Firm* — Patent Jurist; Georgiy L. Khayet

(57) ABSTRACT

In one example embodiment, an alarm unit for monitoring or detecting presence of an analyte on an analyte sensor comprises a square plastic casing protecting the alarm electronics portion and including a signal processing means, a clip attachment means configured to be separated and attached from the casing and used to attach the unit to clothing. The clip attachment has enough clearance to be used with thick articles of clothing including diapers and has a set of teeth frictionally held against a rubber strip portion located on the casing back so as to also enable secure attachment to very thin articles of clothing. The alarm unit may further comprise a three-way switch located externally for easy alarm chime and alarm volume selection. Interdependent modes of operation may enable the signal processing means to control the alarm unit operation and features including low power indication, improper cable plug installment, three-way switch deactivation during Monitor mode, and a snooze/reset feature by which the alarm is disabled temporarily so that, as an example, a user can focus on running to the bathroom where the device is used to treat enuresis.

17 Claims, 24 Drawing Sheets

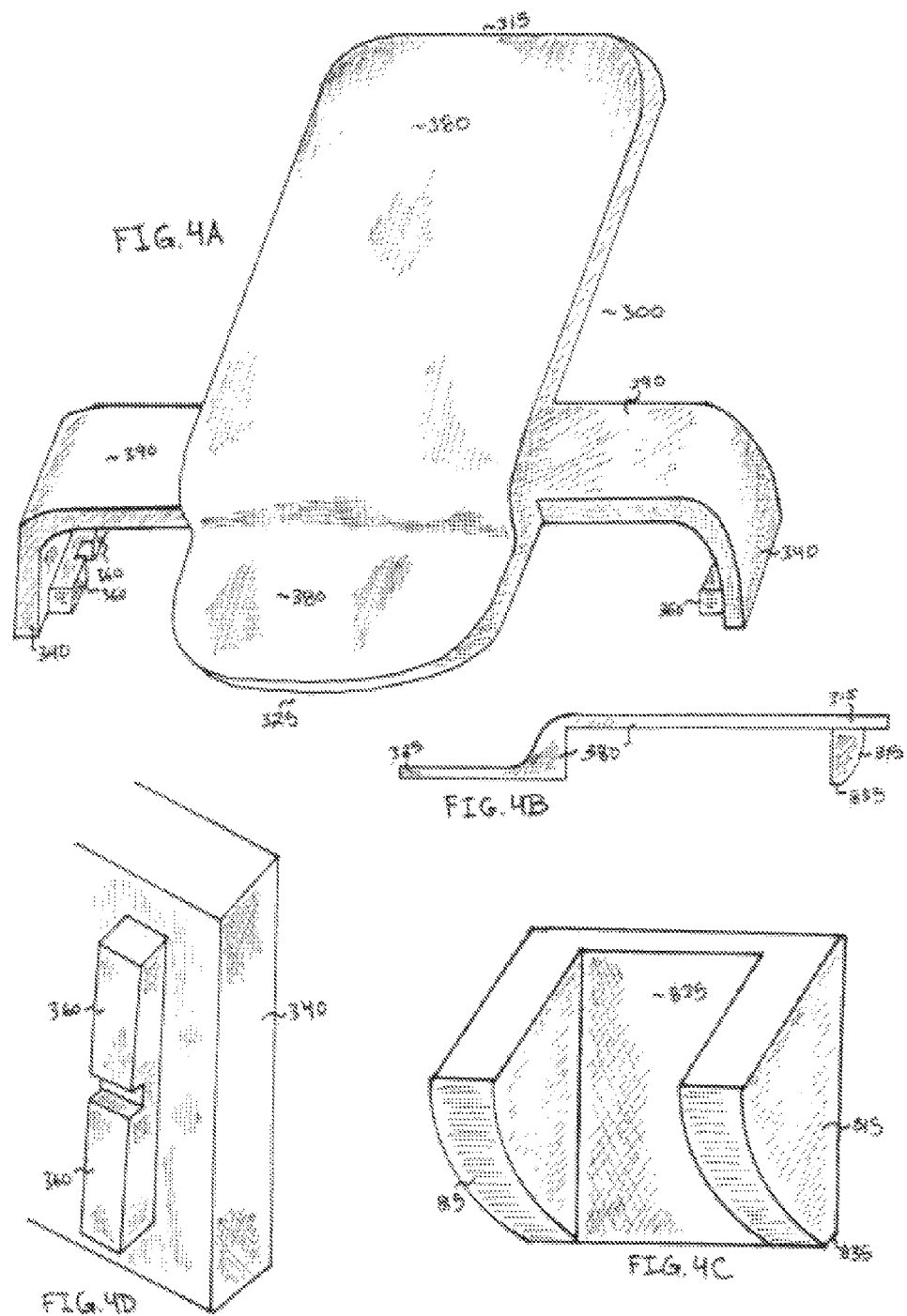

Reset Button

ALARM UNIT FOR MONITORING OR DETECTION OF AN ANALYTE

RELATED APPLICATIONS

This patent application is a Continuation-In-Part application that claims the priority benefit of U.S. Nonprovisional patent application Ser. No. 12/661,823 filed on Mar. 25, 2010 titled "Alarm unit for monitoring or detection of an analyte," which is hereby incorporated by reference in its entirety.

FIELD

The present disclosure relates to devices that alarm and/or monitor the presence of analytes including but not limited to urine. More specifically, but not exclusively, the present disclosure relates to devices for treating enuresis. More specifically, the present disclosure relates to the electronics portion of enuresis alarms including the signal processing portion, the casing surrounding the electronics portion and the means for attaching the casing to articles of clothing in use.

BACKGROUND

The approaches described in this section could be pursued, but are not necessarily approaches that have been previously conceived. Therefore, unless otherwise indicated herein, the approaches described in this section are not prior art to the claims in this application and are not admitted to be prior art by inclusion in this section.

The use of a urine sensor connected by an electrical cable to an electronics portion that may utilize a signal processing unit, for the purpose of treating enuresis is known. Electrolytes present in urine close an alarm circuit thereby indicating micturition. Commonly, the electronics portion may comprise an alarm unit that sounds an alarm and/or vibrates which wakes nocturnal enuresis sufferers. With time, constant waking at the point of micturition enables training the nervous system of the user so as to learn the sensation of needing to urinate. The electronics portion is contained within a casing that is attached to an item of clothing near the user's collarbone.

Various solutions exist for attaching the alarm casing to the user's clothing. Malem Medical of Nottingham, England offers a safety pin permanently attached to the casing. The Dri-Sleeper Excel of New Zealand (described in US 2008/0246620 to Page) offers a hook and tab arrangement which requires each user to sew corresponding hook or tab strips to articles of clothing. US 2005/0110644 to Abramson et al. offers a magnet attached to a flexible arm that extends around a portion of clothing and attaches to a corresponding magnet on the back of the casing.

The above solutions, however, suffer from considerable disadvantages. A safety pin can become dangerously dislodged and needs to be cautiously attached every time. Sewing hook or tab strips to clothing presents a robust but laborious solution; adhesively attaching the corresponding hook or tab to the alarm is not a robust solution. The safety pin and hook and tab solutions also cause the mass of the alarm casing to pull down on the clothing article causing discomfort.

The magnet and arm solution is able to utilize the neck opening of a pajama top, for example, and does not cause uncomfortable pulling on the clothing by virtue of being supported by the neck opening which is supported by the neck of the wearer. Having a strong magnet located in the alarm casing poses special problems however. The above magnetic arm solution to Abramson et al places the controls to the unit inside the alarm casing behind the batteries. Removing the battery door can cause batteries to dislodge and adhere tenaciously to the magnet in the housing making access to the controls difficult. The hook and tab and magnetic arm solution also do not allow for use with a disposable diaper.

The Malem Alarm and Dri-Sleeper Excel (US 2008/0246620 to Page) also place alarm controls inside the alarm casing, presumably exchanging ease of use for the prevention of intentional or unintentional changes to control settings by the user during sleep or alarm event. Indeed, the above US 2008/0246620 to Page requires the user to bridge pins in the circuit board to short out a capacitor in order to cause a change to the frequency of sound.

In use, many existing sensor and alarm unit enuresis devices permit disabling of the alarm by simply pulling out the cable attaching the sensor to the alarm unit. This has the serious disadvantage of a sleepy child being able to easily disable the alarm instead of waking up to clean the sensor and change their underwear and curtails the benefit of alarm therapy. The Malem device above and the Wet-Stop3 offer a two-step shut off feature requiring a sleeping child or other user wake up and remember how to disconnect the sensor plug and then to hold down a silent button for several seconds while the alarm sounds near the ear. This somewhat traumatic wakening distracts the user from focusing on sensations associated with the need to urinate and running to the bathroom to help form the association.

Use of passive electronics at night, whereby the closing of a circuit that activates an electronics unit is done passively as a result of involuntary nocturnal urination, poses special problems. One such problem is knowing if the electronics are operating properly, especially an issue for the child user. The existing solutions in enuresis alarms are void of features that actively confirm whether the sensor is inserted properly, whether the sensor has accidently come off at night or whether the batteries are of insufficient power to operate the alarm. The above disadvantages may result in continual use of a non-functioning enuresis alarm and dissatisfaction and eventual rejection of alarm therapy and may lead to potential misdiagnosis for the cause of enuresis.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

The embodiments described herein may allow overcoming the above-mentioned disadvantages of the existing solutions. A large detachable plastic clip may allow for easy frictional attachment and removal to the shirt collar. The clip may offer enough clearance to be attachable to a thick diaper as needed and may be easily replaced if broken. Detaching the clip may also enable use of alternative attachment means by exposing the casing back. A large external three-way switch may extend outside the housing, may be easy to use and may be protected by a plastic guard portion. Four interdependent power state modes may be employed by a signal processing module to control unit operation.

A Power Up mode may be employed whereby a low power indicator may confirm remaining battery power is sufficient to power the alarm. The signal processing module may then enter the Alarm Setup mode where the three-way switch may be employed to set alarm chime type and alarm volume whereby a zero volume setting may result in vibrate and flashing light only alarm setting. A switch located in the electrical jack may indicate via an alarm that the cable plug leading to the analyte sensor portion has been properly inserted. The switch may be deactivated by the signal processing module after all alarm settings are set in Alarm Setup mode and upon entering Monitor mode. Upon detection of an analyte, the signal processing module may enters Alarm mode whereby a pair of LED lights flash in synchronization with the alarm vibrate and audible alarm per the chime type and volume settings made in Alarm Setup mode. While in Alarm mode, a snooze silent button may be employed allowing the suddenly awakened user to perform one quick simple step to temporarily disable the alarm. The alarm may be disabled for a short period of time making the alarm experience less traumatic and giving the user enough time to go to the bathroom to urinate, clean the sensor and reset the alarm. Various embodiments may also offer known features such as electrode isolation, whereby power is cut off to a sensor unit after detecting urine to prevent dangerous urine electrolysis and alarm lighting, vibration and alarm chime type select and amplification.

The characteristics and utilities of the example embodiments described in this summary and the detailed description below are not all inclusive. Many additional features and advantages will be apparent to one of ordinary skill in the art given the following drawings, specification, and claims.

BRIEF DESCRIPTION OF DRAWINGS

Embodiments are illustrated by way of example and not limitation in the figures of the accompanying drawings, in which like references indicate similar elements and in which:

FIG. 4A is a perspective view of the top side of the clip means, in accordance with an example embodiment.

FIG. 4B is a perspective view of the side of the clip means, in accordance with an example embodiment.

FIG. 4C is an isolated perspective view of the tooth and bridge portion unattached to the clip main body lower end, in accordance with an example embodiment.

FIG. 4D is a perspective view of an attachment arm with tab portions, in accordance with an example embodiment.

FIGS. 5B-1-5B-4 is a diagram of the circuit sub blocks for the alarm unit, in accordance with an example embodiment.

FIG. 5H is a diagram of the Voltage Regulator circuit sub block, in accordance with an example embodiment.

FIG. 5J is a diagram of the Light Emitting Diodes circuit sub block, in accordance with an example embodiment.

DETAILED DESCRIPTION

Example embodiments of are described. In the following description, for purposes of explanation, numerous specific details are set forth in order to provide a thorough understanding of example embodiments. It will be evident, however, to one skilled in the art, that the present invention may be practiced without these specific details.

Figure 1B:
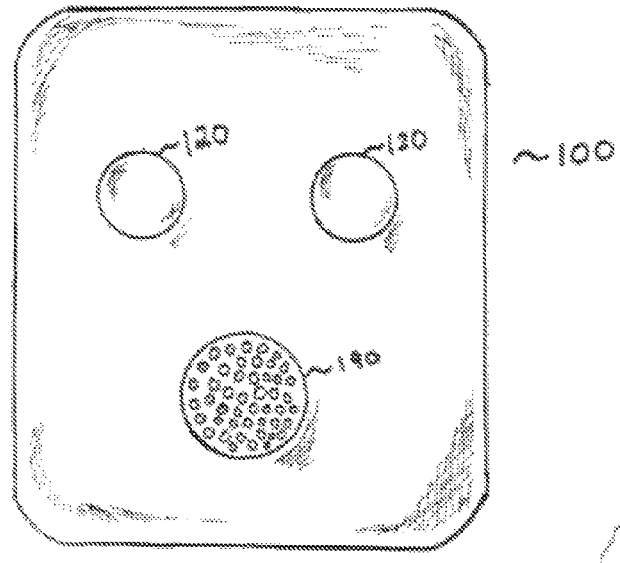
FIG. 1B shows a plain view of the front face of the alarm unit, in accordance with an example embodiment.
Figure 1A:
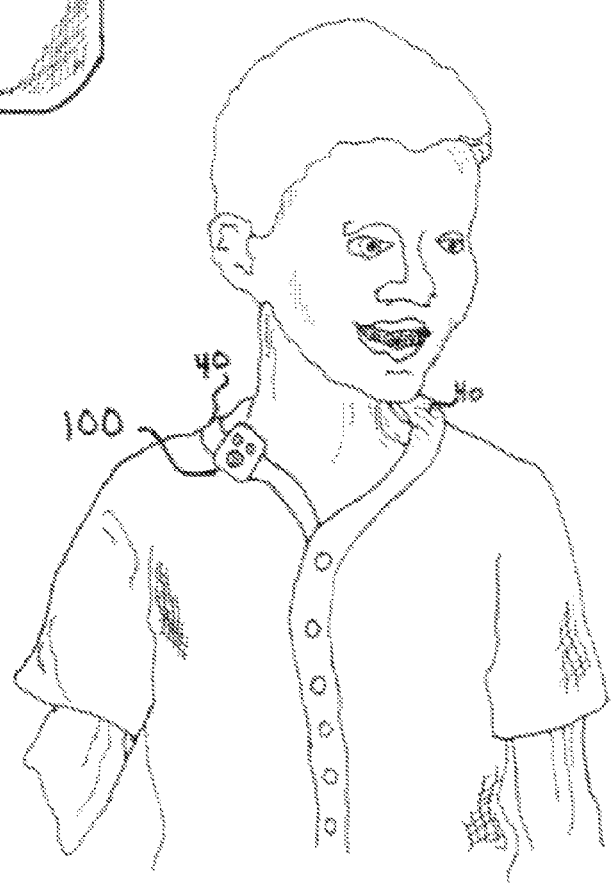
FIG. 1A shows a plain view of the front of the alarm unit as it appears attached to a user's pajama collar, in accordance with an example embodiment.
Figure 2:
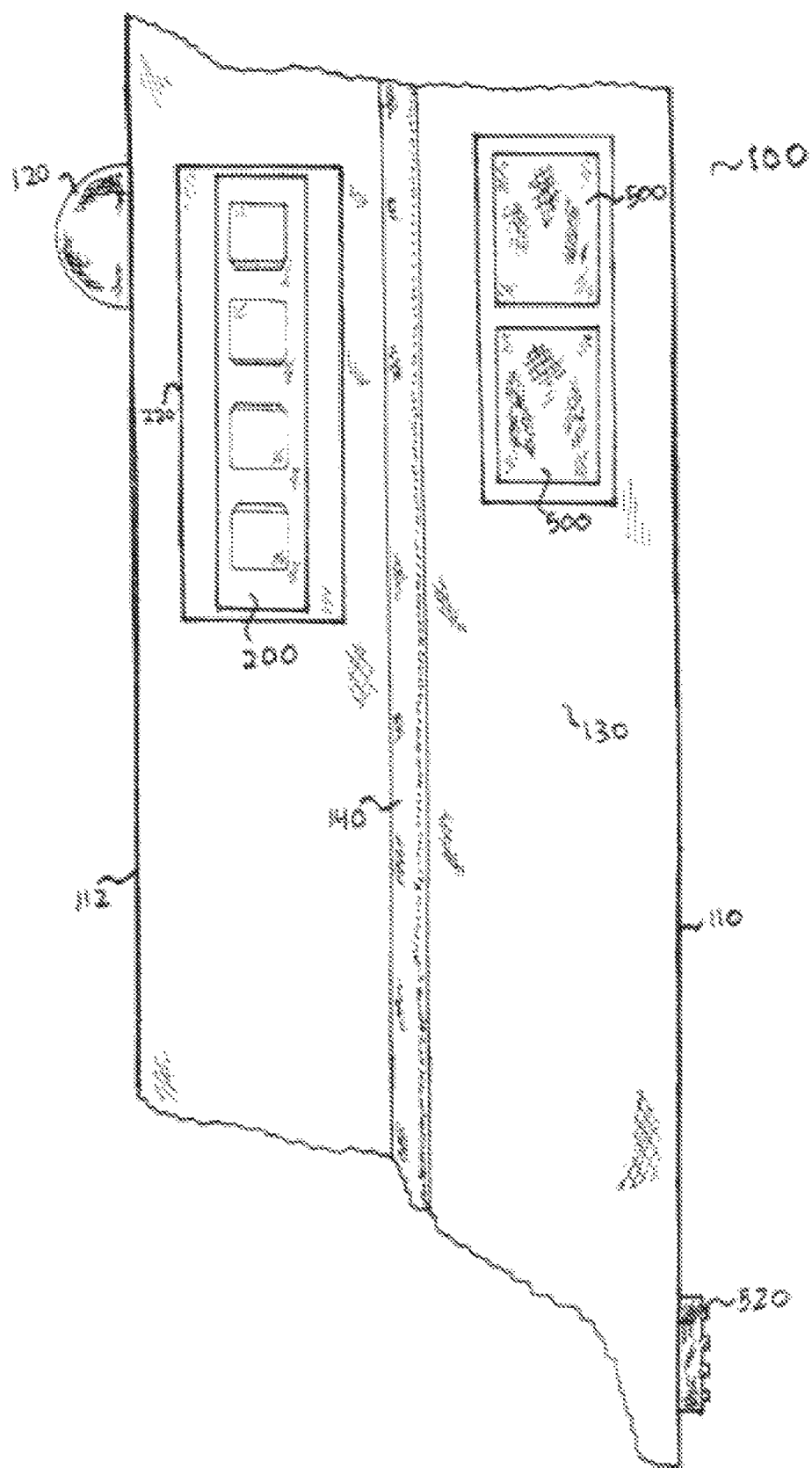
FIG. 2 is a partial side view of the casing displaying the mostly recessed three-way switch handle, an LED light housing, a clip means attachment point and a silicone or rubber strip portion, in accordance with an example embodiment.

FIG. 1A shows a plain view of the front of the alarm unit as it appears attached to a user's pajama collar 40, in accordance with an example embodiment. FIG. 1B shows a plain view of the front face of the alarm unit, in accordance with an example embodiment. FIG. 2 is a partial side view of the casing displaying the mostly recessed three-way switch handle, an LED light housing, a clip means attachment point and a silicone or rubber strip portion, in accordance with an example embodiment. In some example embodiments, an alarm unit may include a power source module, an electronics portion including a signal processing module, a square or rectangular plastic casing 100 surrounding an electronics portion, and a separable clip attachment means.

Figure 3:
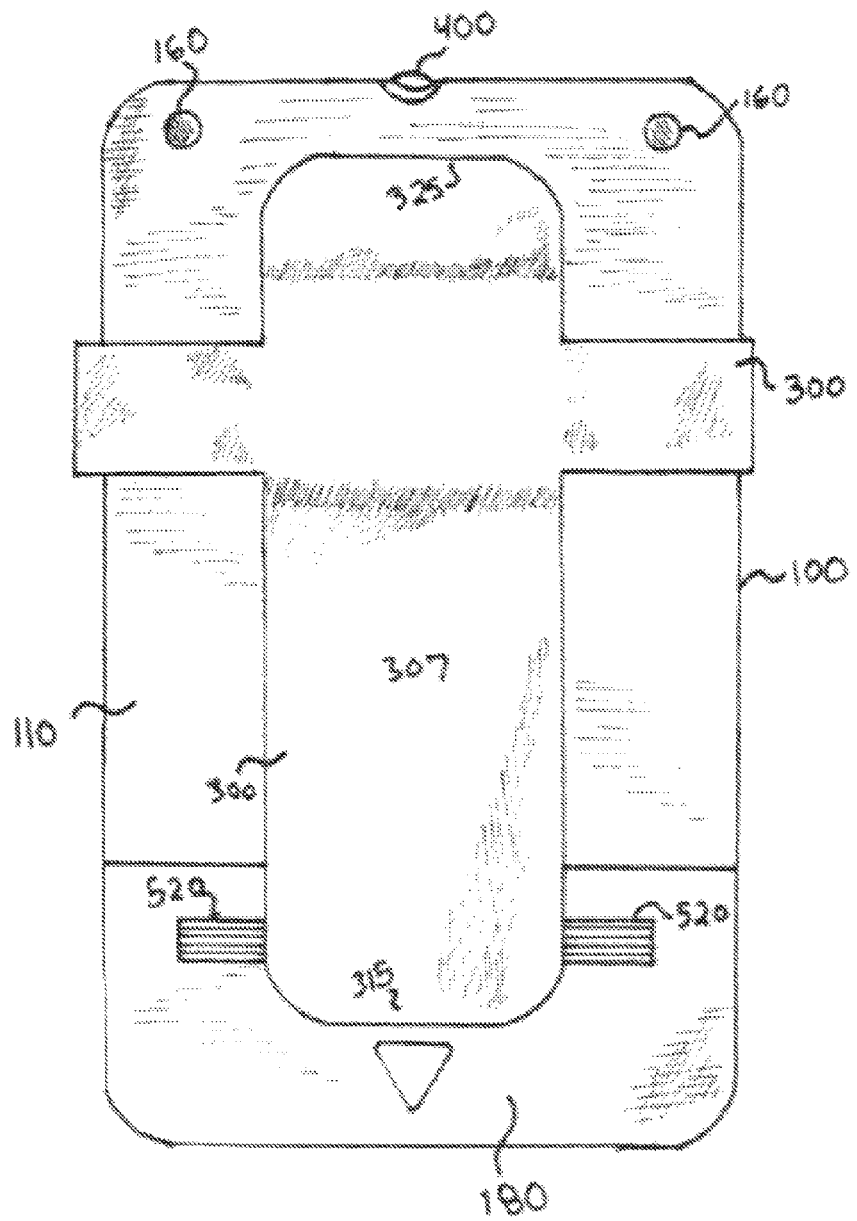
FIG. 3 is a plain view of the back of the alarm unit with the clip means affixed, in accordance with an example embodiment.

FIG. 3 is a plain view of the back of the alarm unit with the clip means affixed, in accordance with an example embodiment. FIG. 4A is a perspective view of the topside of the clip means, in accordance with an example embodiment. FIG. 4B is a perspective view of the side of the clip means, in accordance with an example embodiment. FIG. 4C is an isolated perspective view of the tooth and bridge portion unattached to the clip main body lower end, in accordance with an example embodiment. FIG. 4D is a perspective view of an attachment arm with tab portions, in accordance with an example embodiment.

The plastic casing has front 112 and back 110 main surfaces, left and right sides, and top and lower ends. The front main surface of the plastic casing may include two LED light housings 120 and a perforated alarm grill portion 190. The casing top end may include a recessed snooze silent button 400. The casing back may include a battery door portion 180, a rubber or silicone strip portion 140 and screw holes 160 for attaching the front half of the casing to the back half. Around the periphery of the unit runs a rubber or silicone bumper strip 140 located functionally for the purpose of protecting the electronics in the event of contact with hard surfaces as well as to seal the seam where the casing front half and back half are held against each other via screw attachment means. The casing left and right sides may include small slot means 500 and a switch guard lip portion 220 for the three-way switch 200. A power source means may include batteries.

In a preferred embodiment, a large detachable plastic clip means 300 may be attachable via the left and right slot means 500 on the right and left sides of the plastic casing that correspond to left and right tab means 360 on the ends of two attachment arms 340. The clip means 300 may comprise a vertical main body portion 380 and a horizontal casing attachment portion 390 wherein the two portions are attached to each other in a perpendicular configuration with the main body upper end 325 extending above the horizontal top edge of the casing attachment portion 390 and the main body lower end 315 extending below the horizontal bottom edge of the casing attachment arm portion 340.

The main body lower end portion 315 may occupy a plane that is parallel to but above the plane occupied by the main body upper end 325, wherein the main body lower end plane 325 is located farther away from the casing back than that plane occupied by the main body upper end 315. The plane occupied by the main body lower end 325 being of sufficient distance from the casing back to enable using the clip on thick types of clothing such as diapers. The casing attachment portion 390 may comprise two opposite attachment arms 340 that extend outward and then downward from the clip main body portion 380. On the inner surface of the downward extending portion of the attachment arms are a pair of tab means 360 that attach frictionally into slot means 500 located on the left and right sides of the casing 100.

Attached to the clip main body bottom surface lower end are a set of parallel plastic semicircular teeth 815 that extend downward from the bottom side of the main body and terminate in a tip end. A tooth bridge portion 825 extends perpendicularly to and is attached between and to the parallel teeth 815 so that the parallel teeth support the tooth bridge portion. The tip ends of the parallel teeth and bottom surface of the tooth bridge are aligned so as to form an elongated contact point 835 for crimping a portion of clothing, for example a pajama top collar 40, between the elongated contact point and a rubber strip portion 520 located permanently on the casing back. The elongated contact point 835 is comprised of roughened plastic so that even thin portions of clothing will not slip around between the elongated contact point 835 and rubber strip 520.

The elongated contact point and the rubber strip are forced together by the positioning of the slot and tab attachment means and the clip main body upper end which lies flat against the surface of the casing back. The positioning enables the attachment arms to act as a fulcrum, so that the clip main body upper end supports the attachment arms when the elongated contact point is lifted away from the casing back to crimp a portion of clothing against the rubber strip.

In an alternative embodiment, the clip means is not used whereby the casing back is exposed for use with other means for attaching the casing to the user's clothing. The clip remains a preferred embodiment, however, due its ease of use, robustness, use with any thickness of clothing article including diapers, and because it allows for the unit to be very easily transported from one article of clothing to another.

Figures 1, 5A:
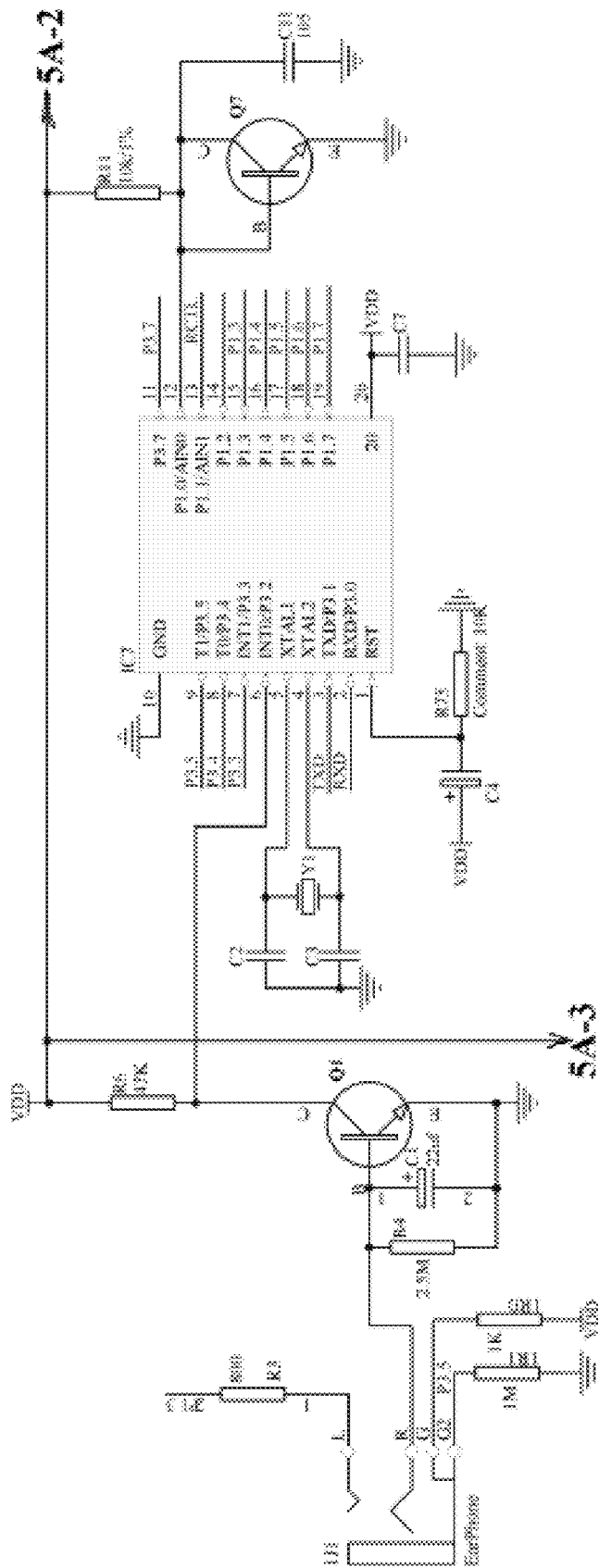
FIGS. 5A-1-5A-4 is a circuit diagram for the alarm unit, in accordance with an example embodiment.
Figures 2, 5A:
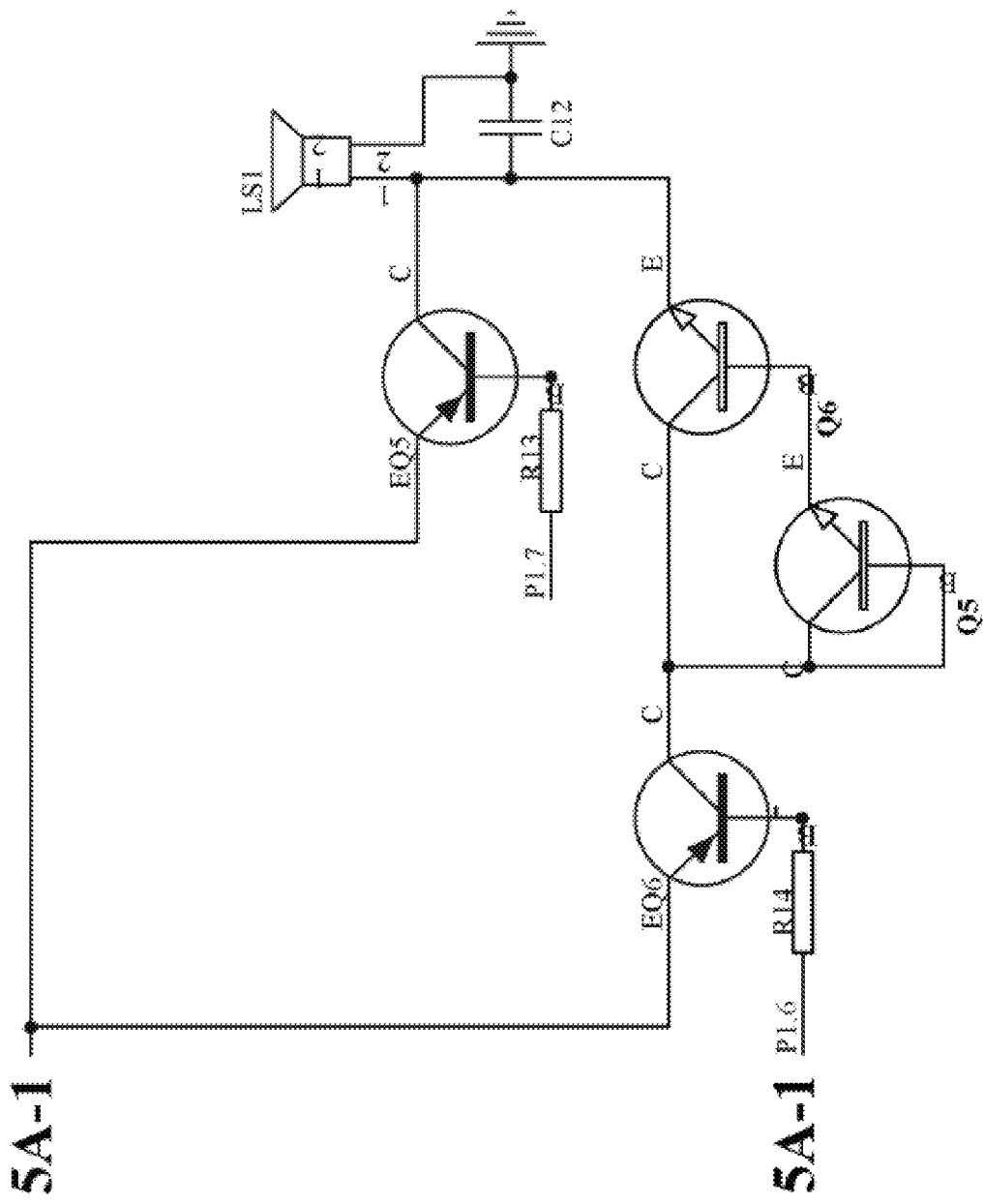
Figures 3, 5A:
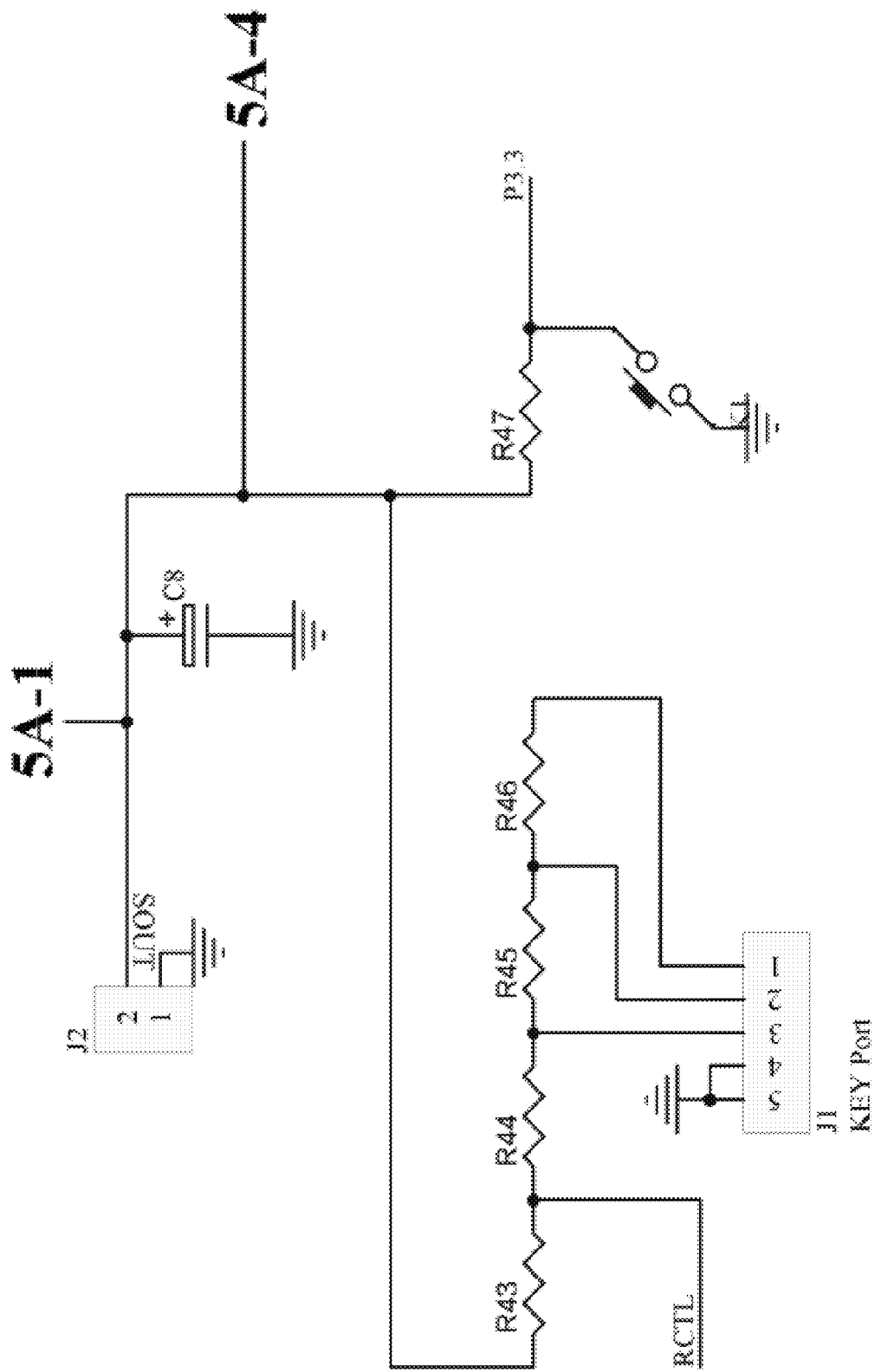
Figures 4, 5A:
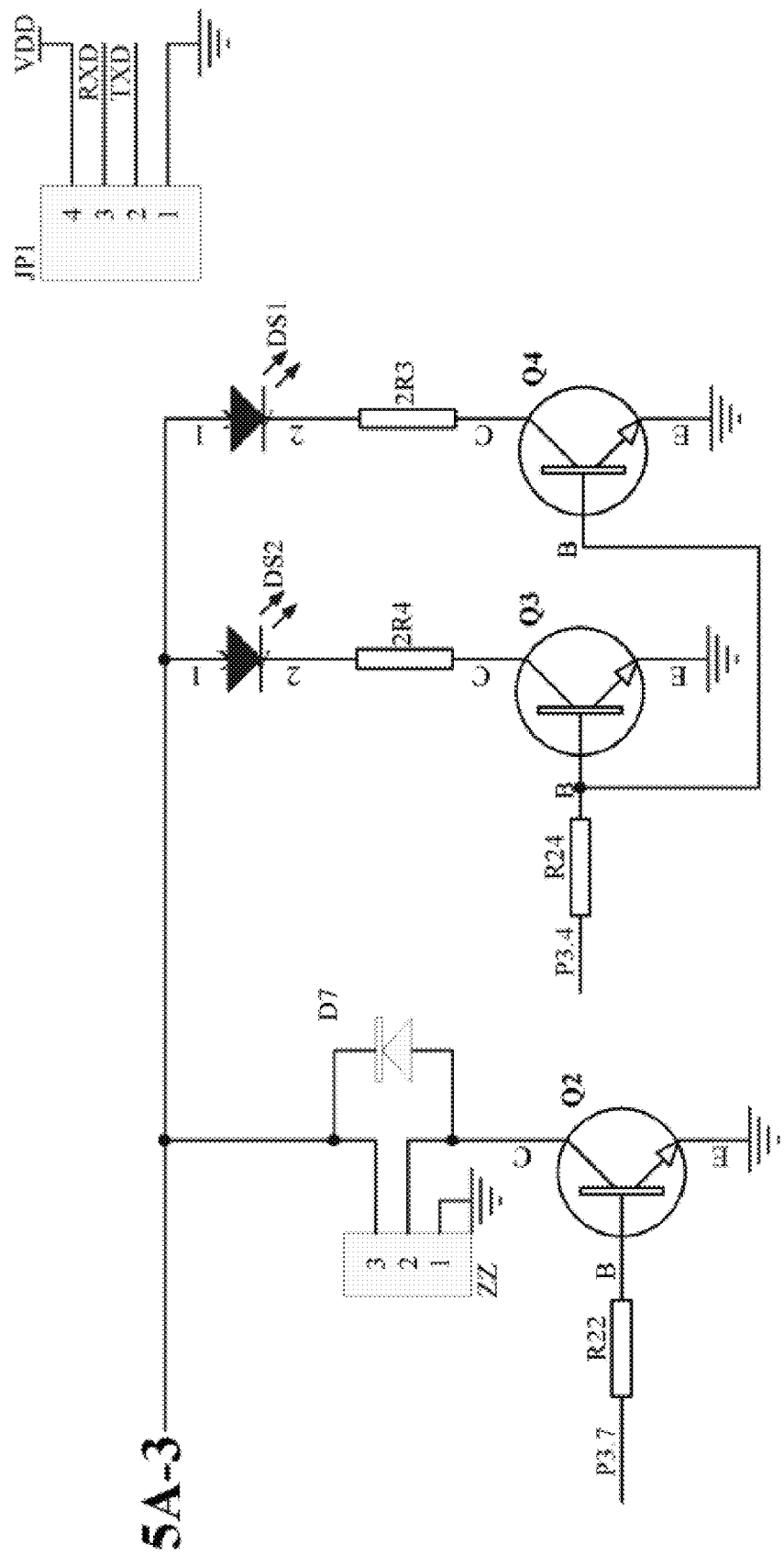
Figures 1, 5B:
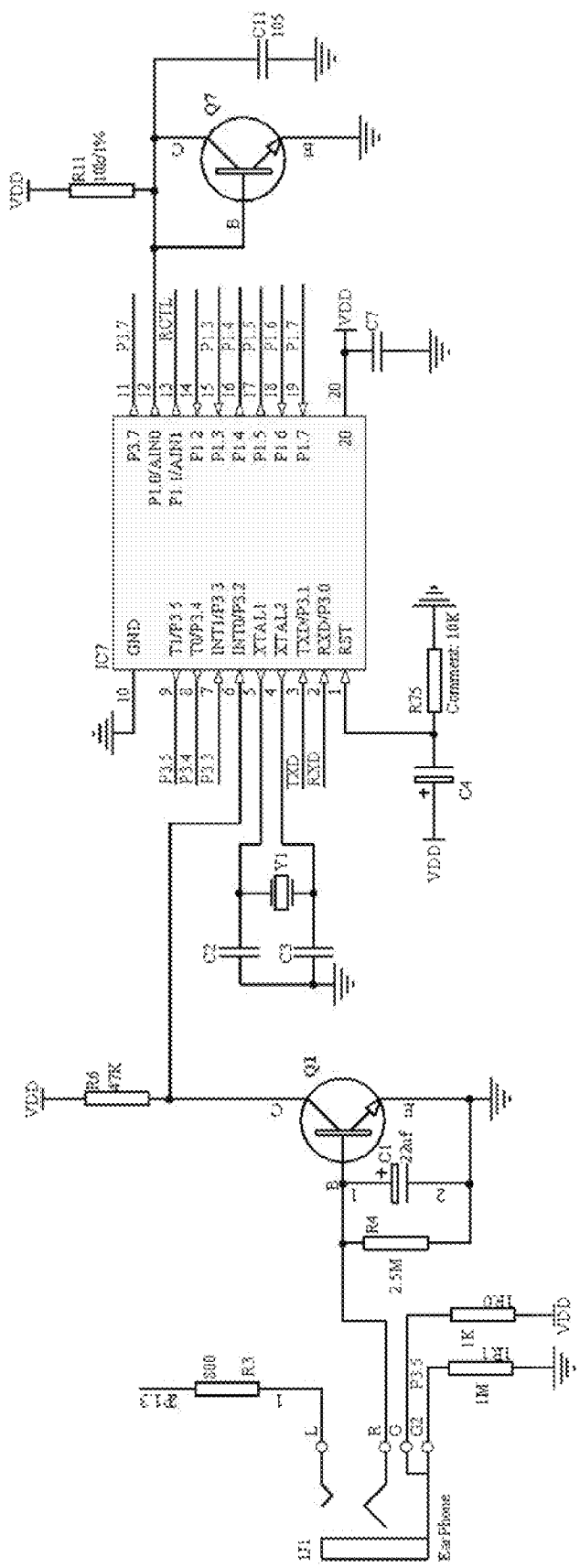
Figures 2, 5B:
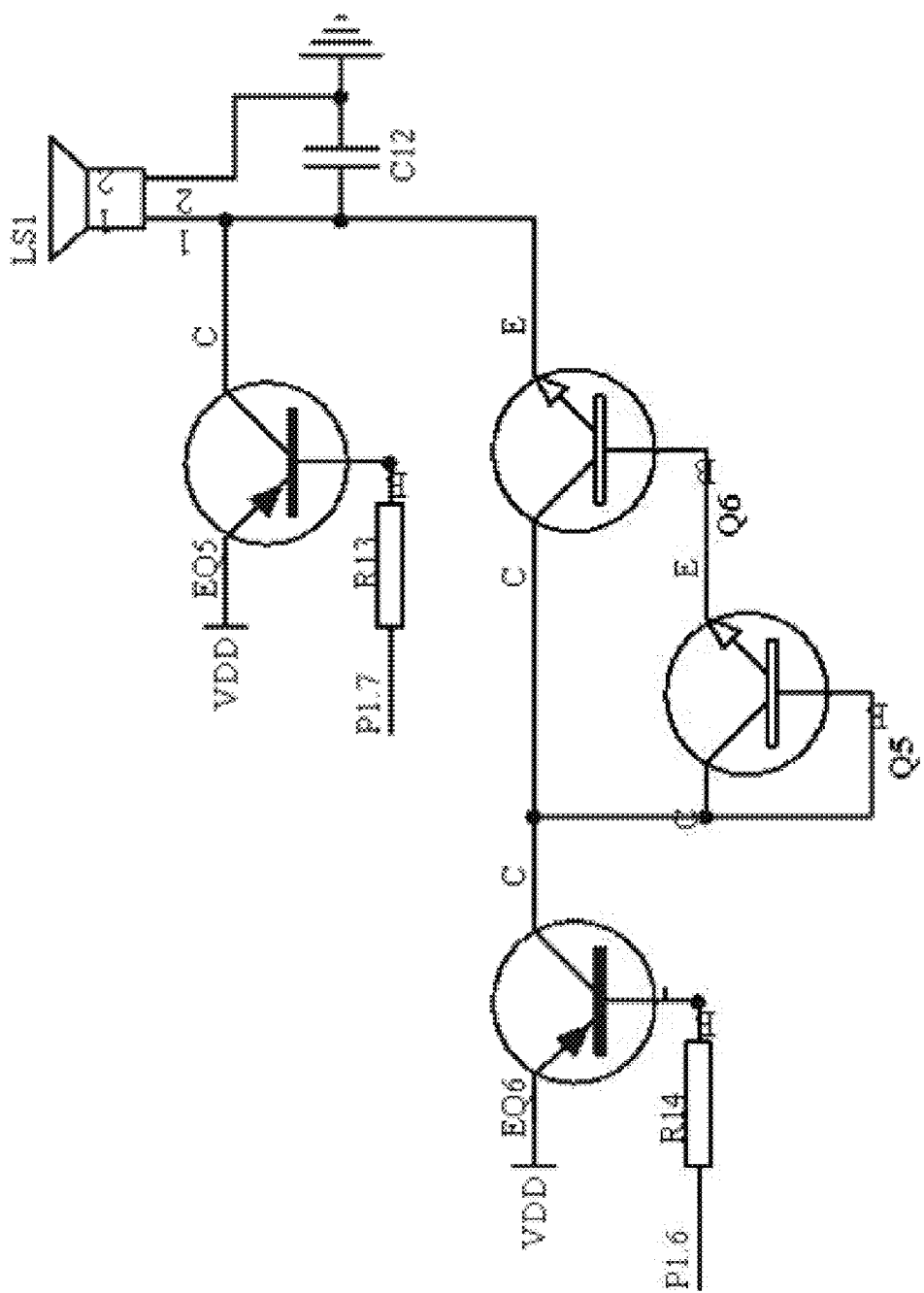
Figures 3, 5B:
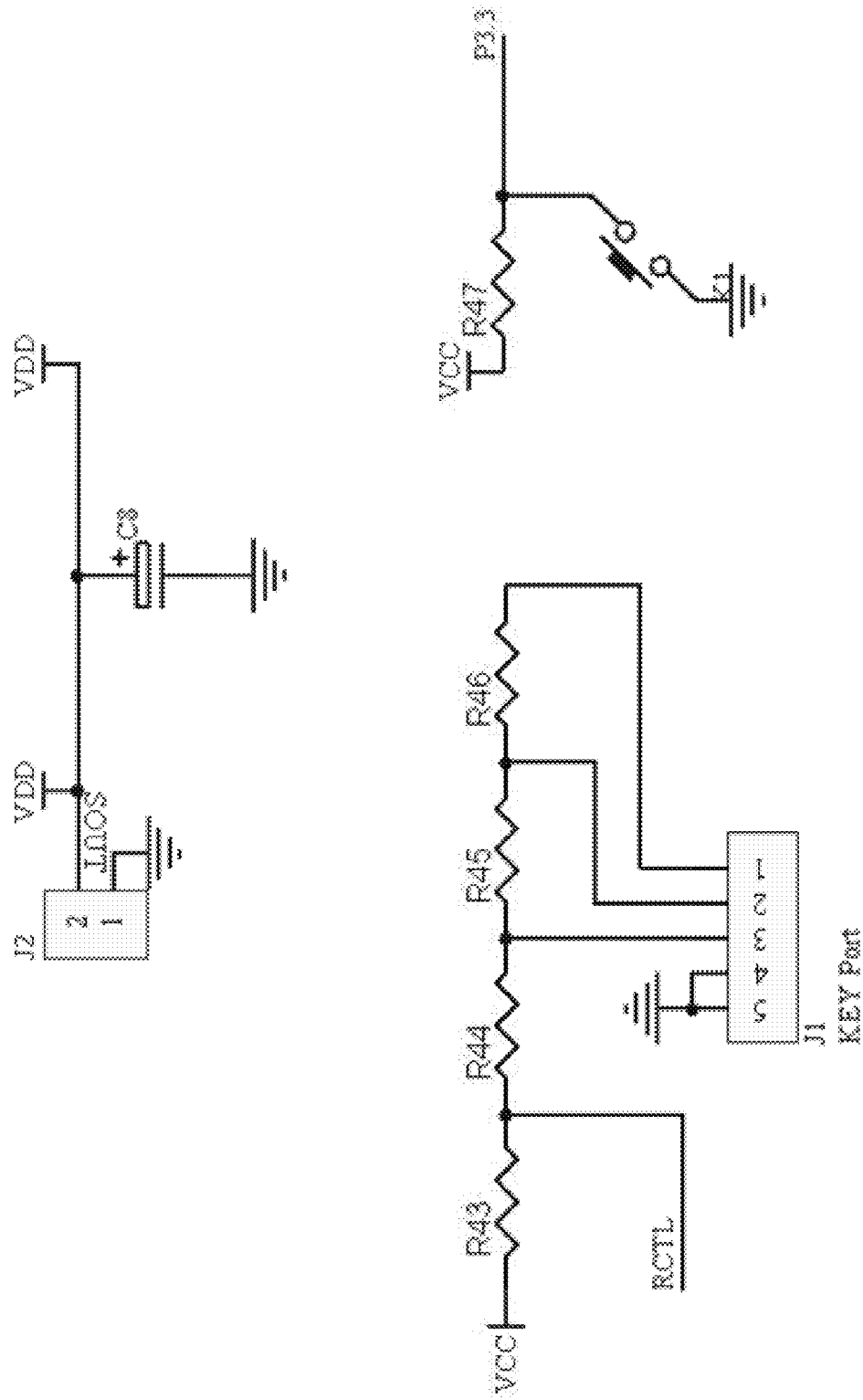
Figures 4, 5B:
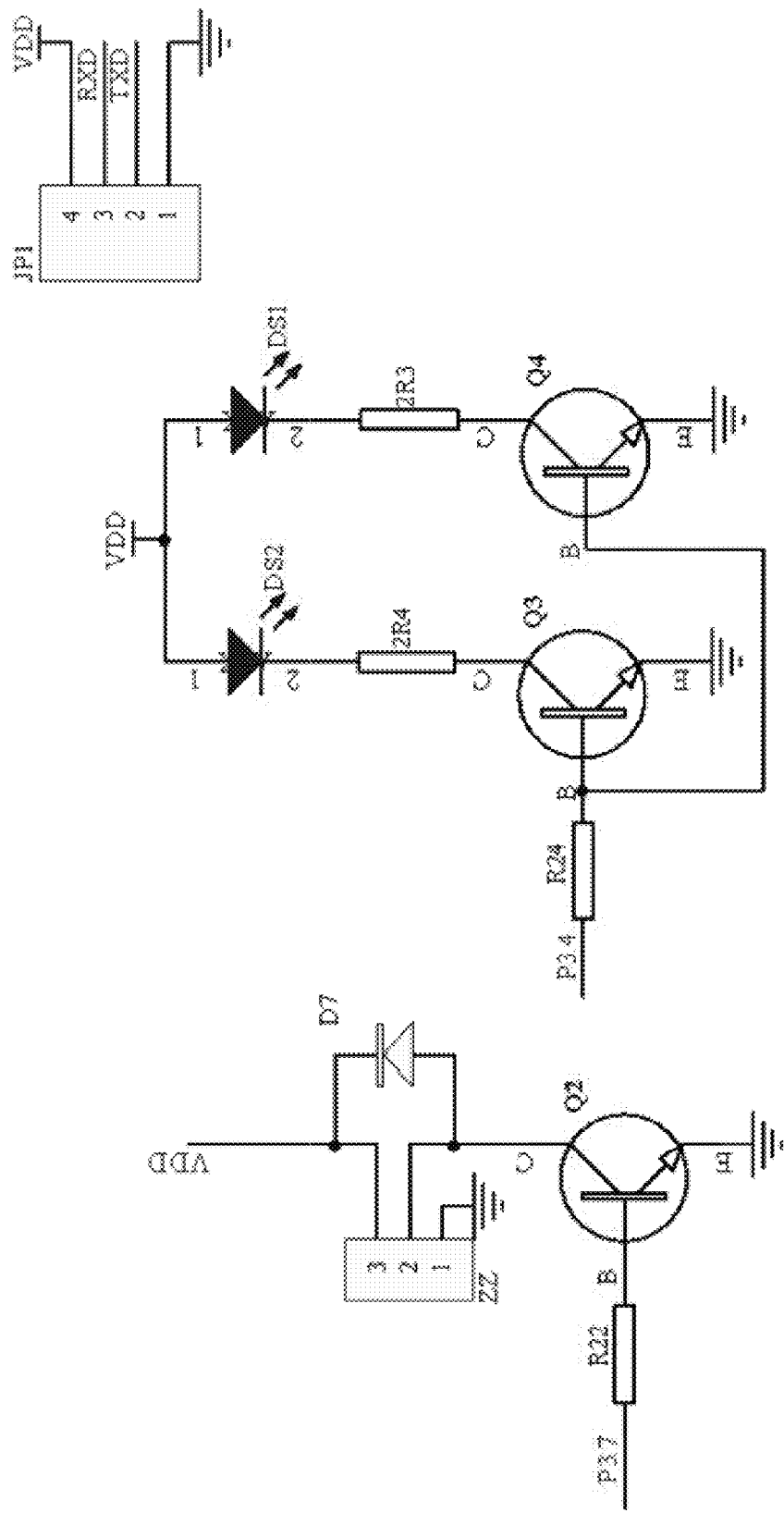
Figure 5C:
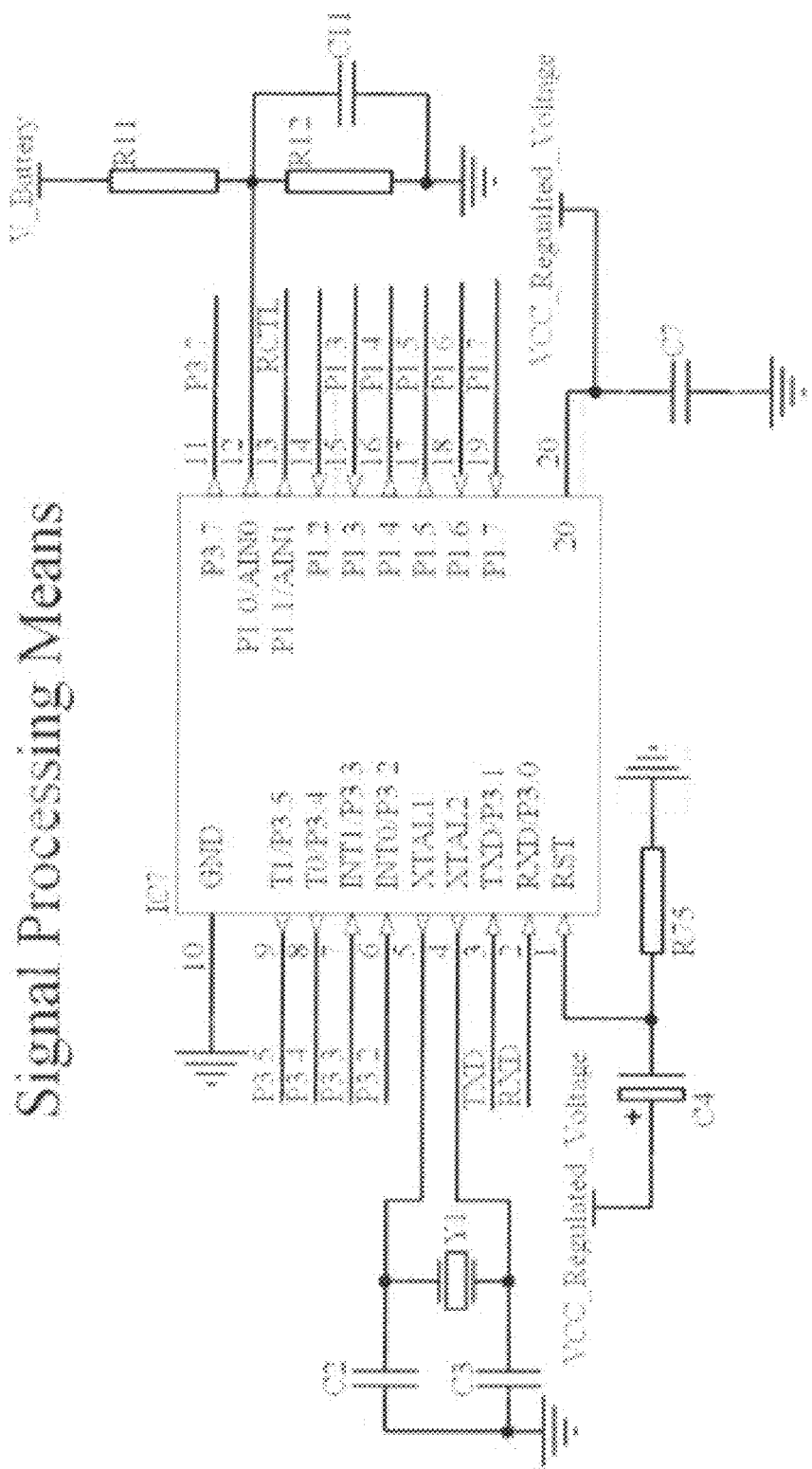
FIG. 5C is a diagram of the Signal Processing Means circuit sub block, in accordance with an example embodiment.
Figure 5D:
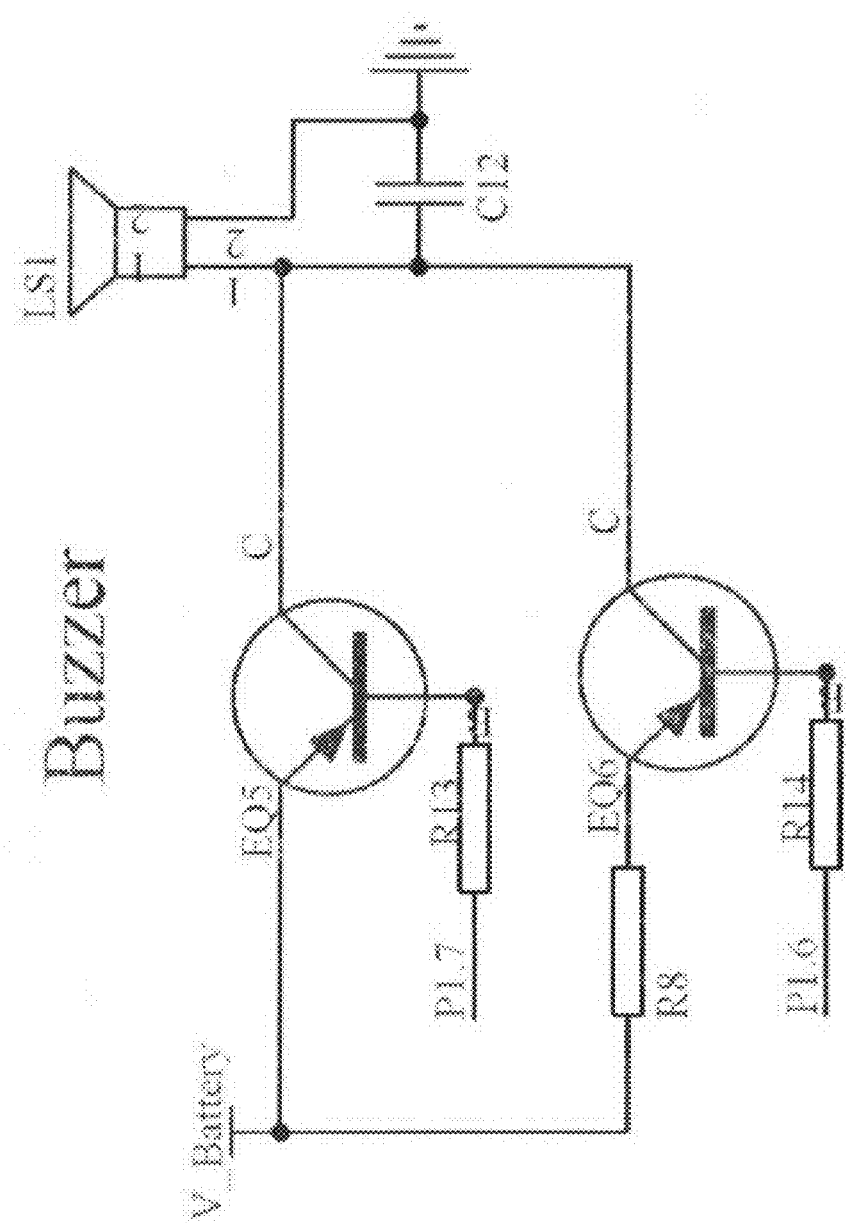
FIG. 5D is a diagram of the Buzzer circuit sub block, in accordance with an example embodiment.
Figure 5E:
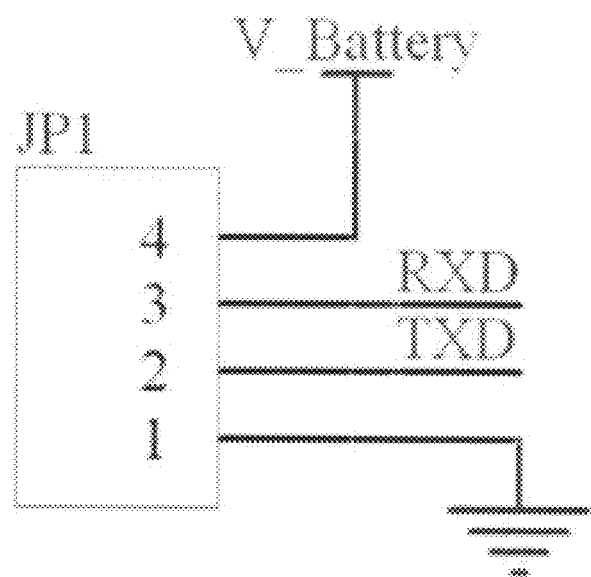
FIG. 5E is a diagram of the Communications Port circuit sub block, in accordance with an example embodiment.
Figure 5F:
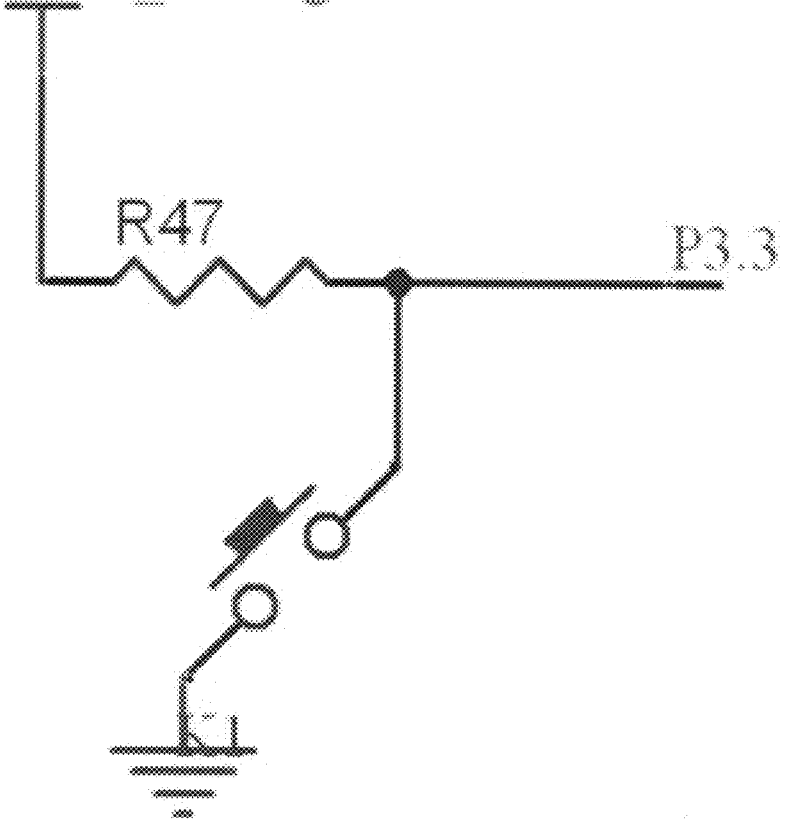
FIG. 5F is a diagram of the silent or reset button circuit sub block, in accordance with an example embodiment.
Figure 5G:
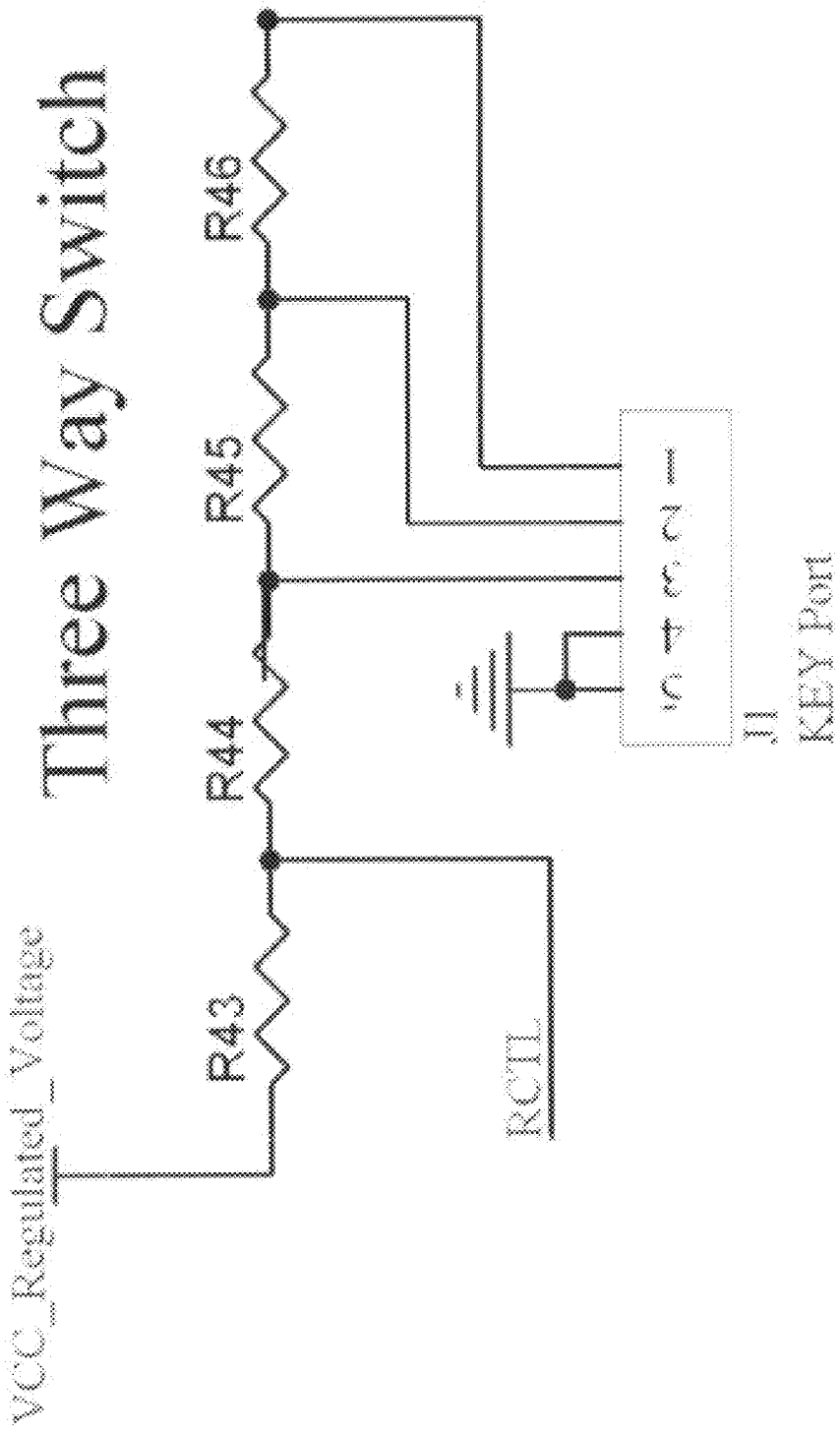
FIG. 5G is a diagram of the Three Way Switch circuit sub block, in accordance with an example embodiment.
Figure 6H:
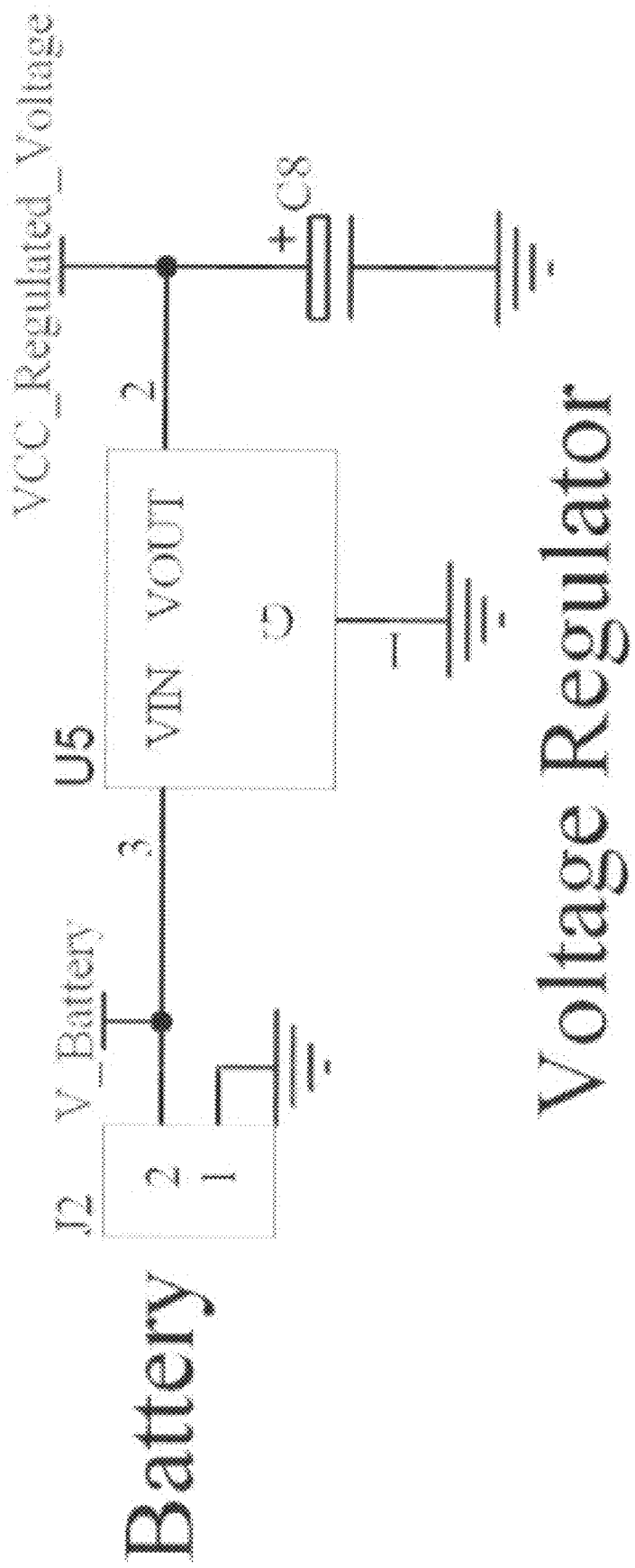
FIG. 6A-6C are flowchart diagrams depicting the modes of operation and the power state modes, in accordance with an example embodiment.
Figure 5I:
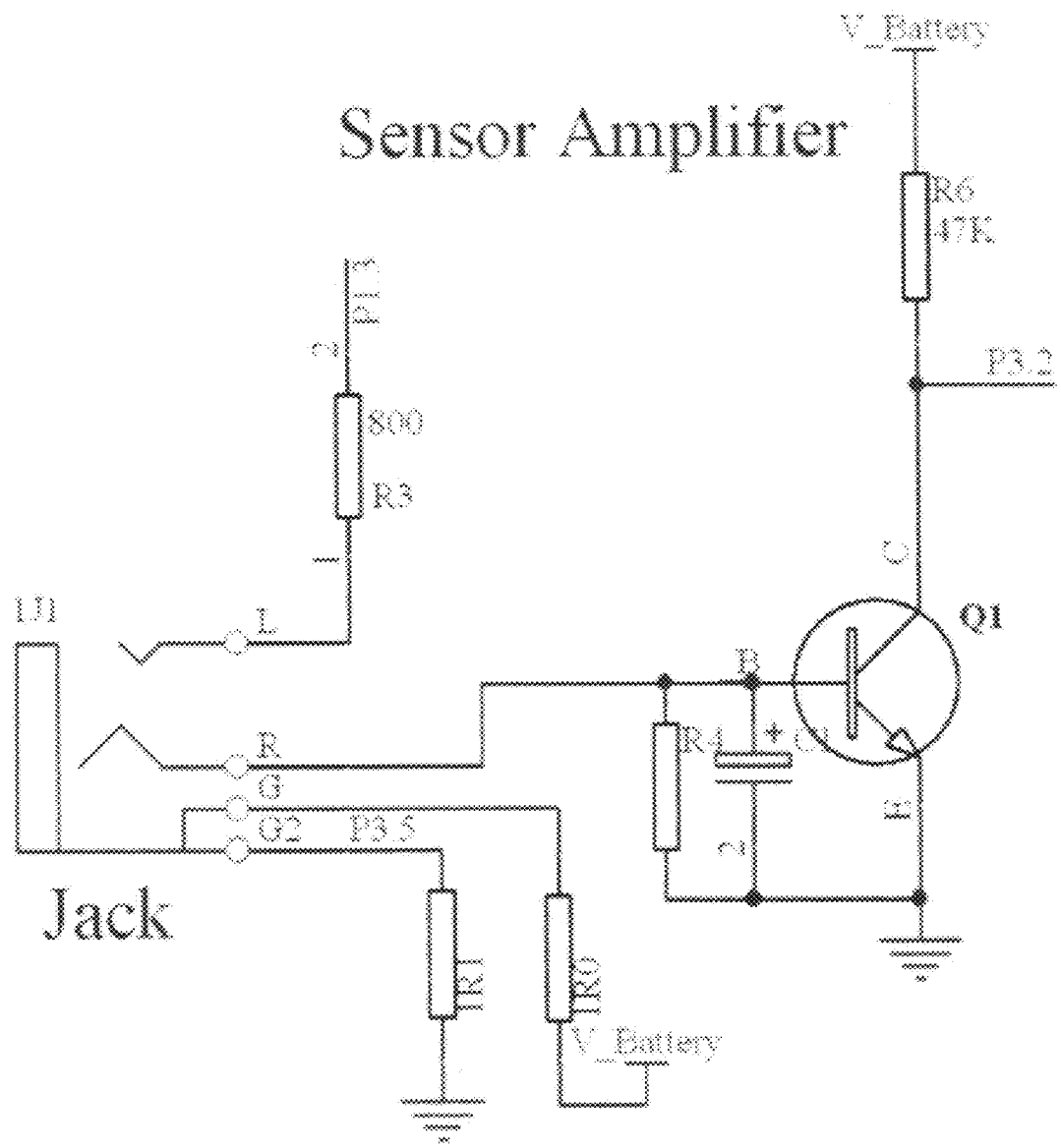
FIG. 5I is a diagram of the Sensor Amplifier circuit sub block, in accordance with an example embodiment.
Figure 51:
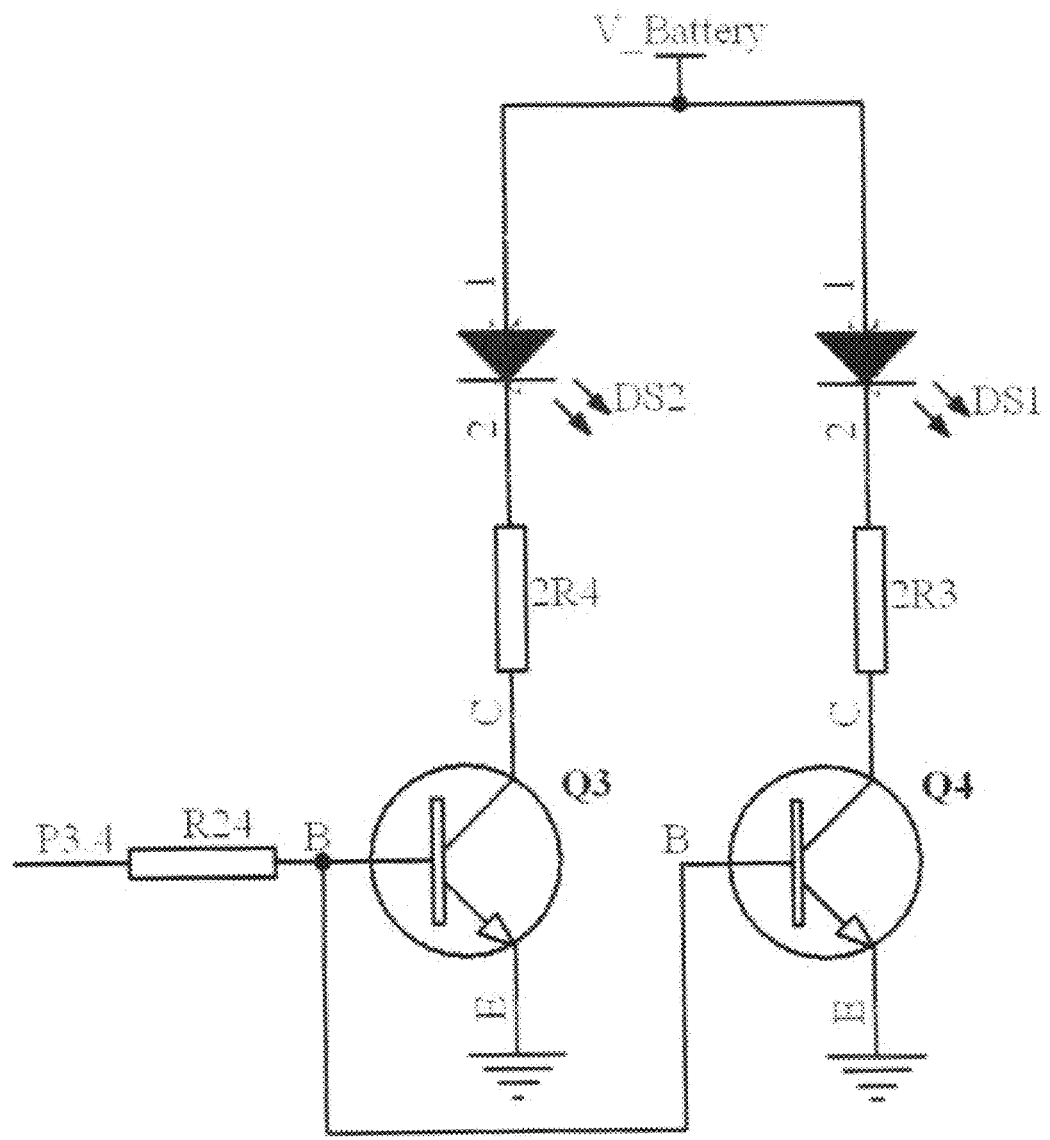

FIGS. 5A-1-5A-4 is a circuit diagram for the alarm unit, in accordance with an example embodiment. FIGS. 5B-1-5B-4 is a diagram of the circuit sub blocks for the alarm unit, in accordance with an example embodiment. FIG. 5C is a diagram of the Signal Processing Means circuit sub block, in accordance with an example embodiment. FIG. 5D is a diagram of the Buzzer circuit sub block, in accordance with an example embodiment. FIG. 5E is a diagram of the Communications Port circuit sub block, in accordance with an example embodiment. FIG. 5F is a diagram of the Silent button circuit sub block, in accordance with an example embodiment. FIG. 5G is a diagram of the Three Way Switch circuit sub block, in accordance with an example embodiment. FIG. 5H is a diagram of the Voltage Regulator circuit sub block, in accordance with an example embodiment. FIG. 5I is a diagram of the Sensor Amplifier circuit sub block, in accordance with an example embodiment. FIG. 5J is a diagram of the Light Emitting Diodes circuit sub block, in accordance with an example embodiment.

Figure 5K:
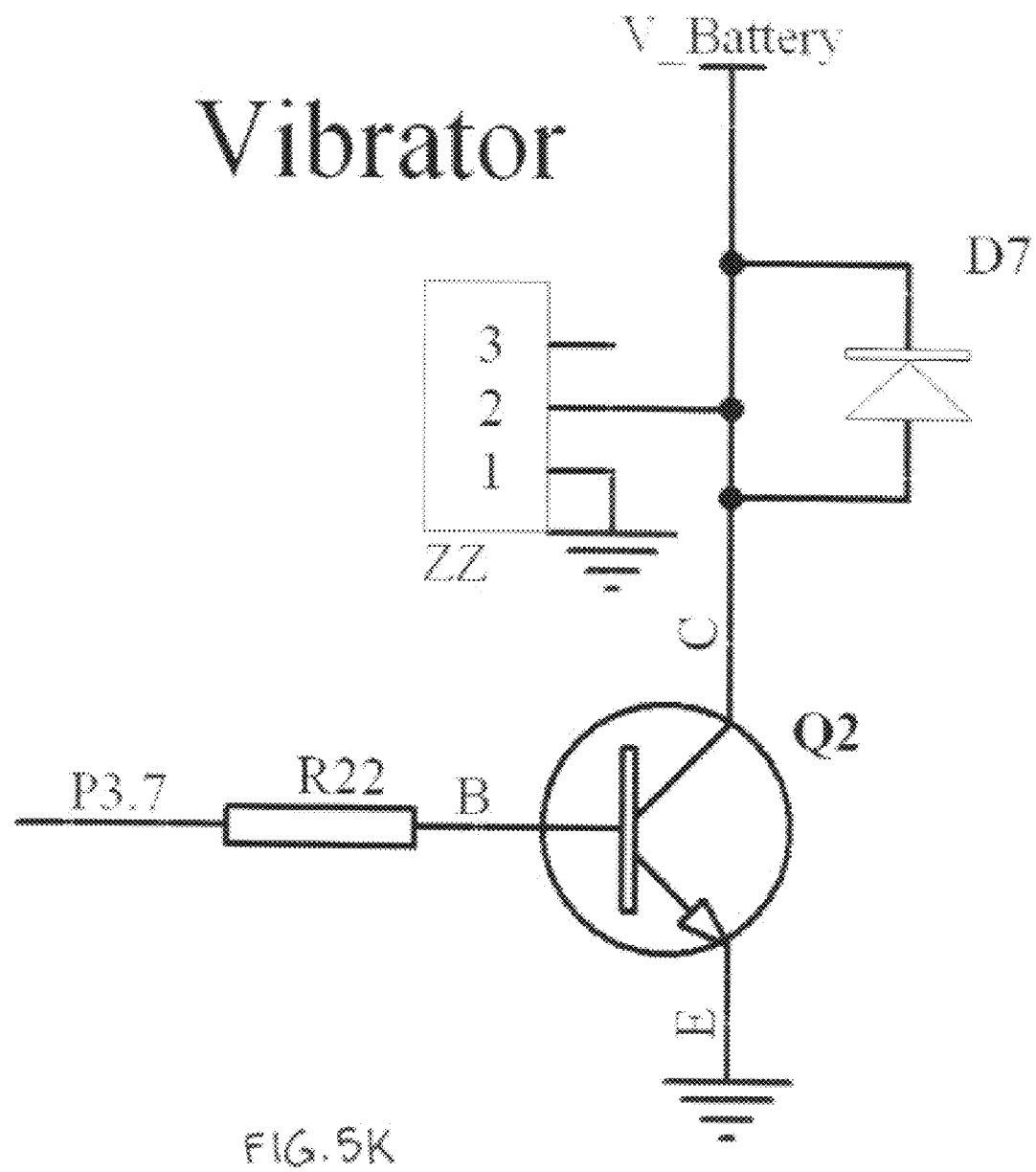
FIG. 5K is a diagram of the Vibrator circuit sub block, in accordance with an example embodiment.
Figure 6A:
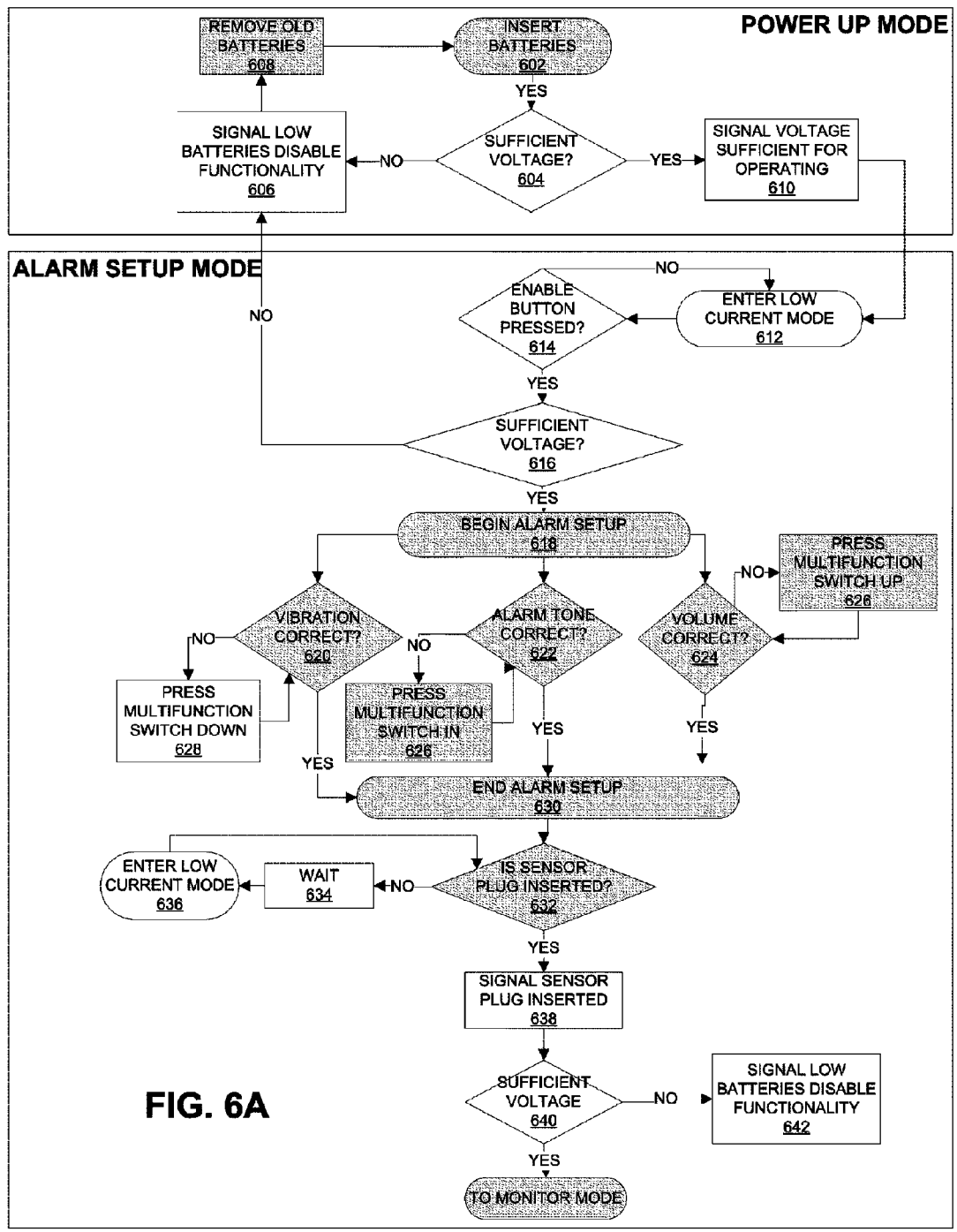
Figure 6B:
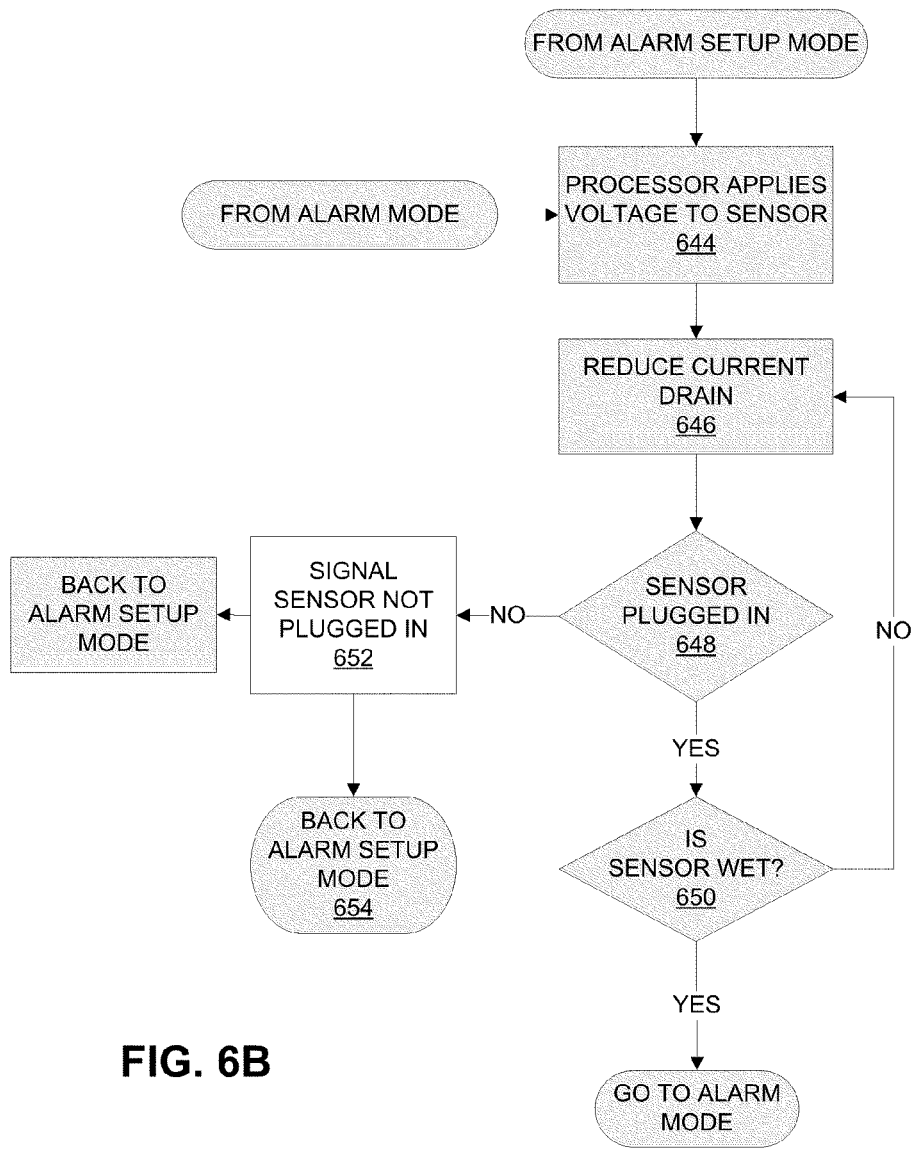
Figure 6C:
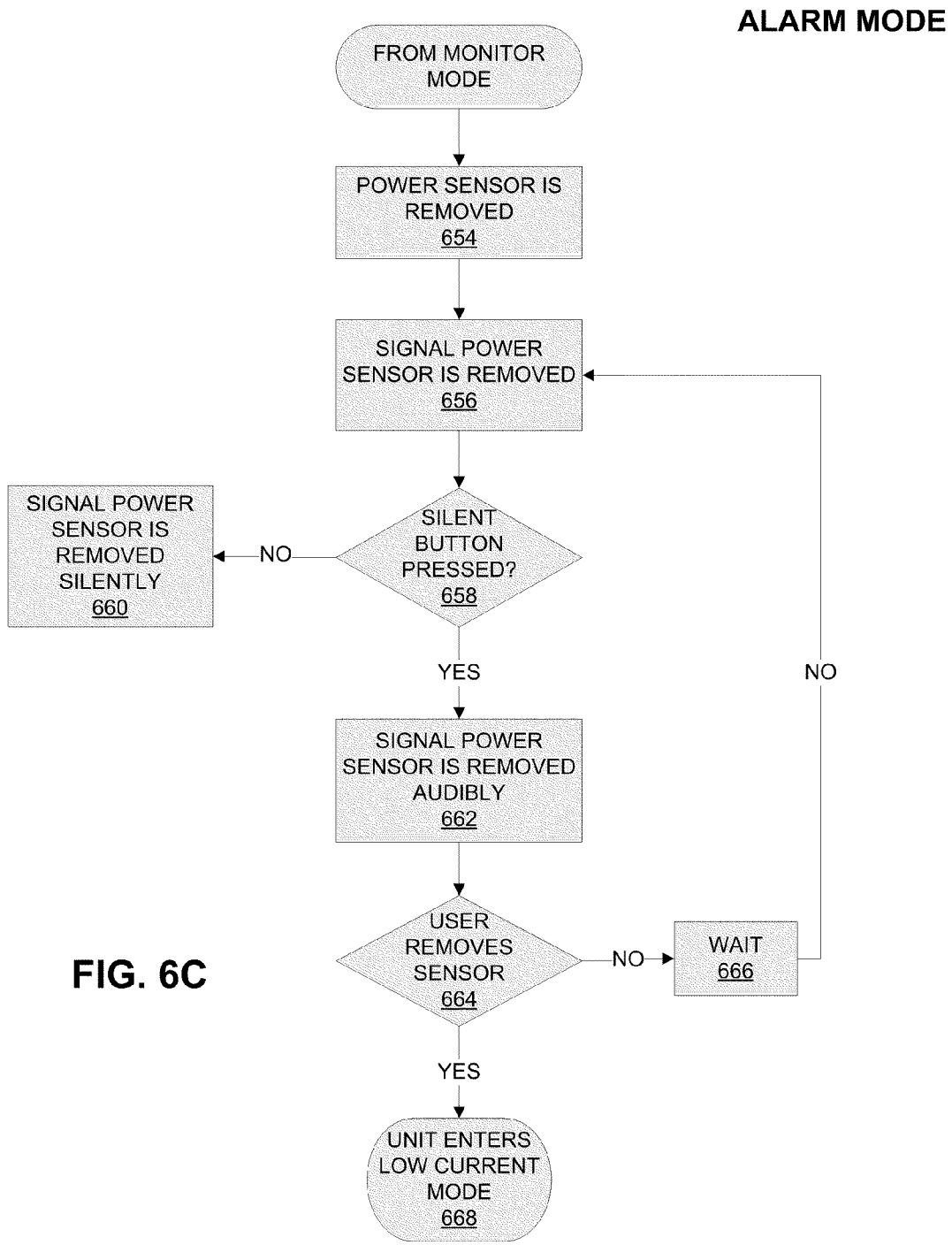

FIG. 5K is a diagram of the Vibrator circuit sub block, in accordance with an example embodiment. FIG. 6A-6C are flowchart diagrams depicting the modes of operation and the power state modes, in accordance with an example embodiment.

The signal processing means may operate, in a non-limiting sense, in four interdependent modes so as to control unit operation and to properly employ certain features. Upon installment of batteries the first mode entered is the Power Up mode.

During the Power Up mode the signal processing means may establish that there is sufficient power in the batteries to activate the alarm. This low power indicator feature may be implemented in the software controlling the signal processing means. Within the signal processing means there are one or more analog to digital converters. The analog to digital converter may be connected to the battery Voltage through a programmed multiplexer. The output of the analog to digital converter may be compared to a programmed digital word. This digital word may comprise a specific number of bits. If the output of the analog to digital converter is less than that of the programmed digital word, the low power alarm may be enabled including sending power to audible alarm means and light emitting means. The low power alarm has sufficient priority to interrupt other programs running on the signal processing means.

An example workflow may commence at operation 602 with a customer inserting batteries into the device. Accordingly, the device may enter the power up mode. At decision block 604, the battery power may be measured, compared to a predetermined value, and, based on the comparison; a decision may be made as to whether the battery has sufficient power to operate. For example, according to predetermined value, the battery voltage below 2.3 can be considered insufficient to power the alarm unit. If it is determined that the battery power is insufficient, a low voltage alarm may sound at operation 606. For example, the LEDs may blink fast five times and the unit may beep fast five times. The low battery alarm may repeats after every 60 seconds and may continue until the batteries are replaced. At the same time, functionalities of the alarm unit may be impaired. For example, the three-way switch and the silent button may be disabled. If low battery voltage is detected, old batteries may be removed at operation 608 and new batteries installed at operation 602. After determining sufficient power supply, the signal processing means enters Alarm Setup mode wherein the alarm settings are made using the three-way switch and wherein a switch means within the electric jack portion of the electronics portion indicates whether the 3.5 mm cable plug from the electrical cable leading to and from the analyte sensor portion has been properly inserted. The switch means is located within the 3.5 mm electric jack portion.

An input pin to the signal processing means is connected to the output of the switch that is located on the 3.5 mm jack. The output of the switch is connected to a resistor which is connected to the negative supply. The switch is connected to the positive supply. When the 3.5 mm plug is inserted into the jack (analyte sensor installed) the switch is open. With the sensor plugged into the jack the output of the switch is the negative supply. If the sensor is not plugged into the 3.5 mm jack the output of the switch is connected to the positive supply. The signal processing means input pin receives either a positive supply input and enables the sensor unconnected alarm involving the light emitting means and audible alarm means. The sensor unconnected alarm is implemented in the software controlling the signal processing means.

Protruding slightly from the surface of the casing side is the three-way switch handle 200, protected all around by a switch guard portion 220 that operates as a protective lip. The switch handle is semicircular and contains ridges for easy switch manipulation with the finger and/or fingernail. The three-way switch consists of three switches. One contact of each switch in the three way switch is connected to a resistor. The other contact of each switch is connected to the positive supply. When a switch is used, a signal processing means input pin becomes connected to various voltages of different values. The programming software of the signal processing means controls the actions of the output pins with the application of the positive supply to each respective input pin. In use, the three-way switch is employed only in the Alarm Setup mode whereupon the switch is used to toggle through and select an alarm chime type and to select alarm volume with a zero volume setting of no audible alarm so that only vibrate and lights are used to alarm analyte detection. After both chime type and volume have been set using the three-way switch the signal processing means exits the Alarm Setup mode and enters Monitor mode and in doing so deactivates the three-way switch whereby the alarm settings cannot be changed accidentally.

If, on the other hand, the correct battery power is detected, the workflow may proceed to signal power sufficiency at operation 610. For example, to indicate that the power source has sufficient voltage to operate the alarm unit, the alarm unit may beep and flashes LEDs (e.g., one beep and flash for one second). Additionally, the sound level for alarms in power up mode is set to maximum. Once the test power has been successful, the workflow may proceed to the alarm setup mode.

At operation 612, the workflow may enter a low current mode. The low current mode may be entered whenever the unit is not in alarm setup mode. The enable button may be pressed at operation 614. If the sensor is inserted, the unit will not be able to enter the alarm configuration mode. Because the battery power may still deplete while in the unit is the low current mode, at decision block 616 the battery power may be measured, compared to a predetermined value, and, based on the comparison, a decision may be made as to whether the battery has sufficient power to operate. If it is determined that the battery power is insufficient, a low voltage alarm may sound at operation 606. For example, the LEDs may blink fast five times and the unit may beep fast five times. The low battery alarm may repeat after every 60 seconds and may continue until the batteries are replaced. At the same time, functionalities of the alarm unit may be impaired. For example, the three-way switch and the silent button may be disabled. If low battery voltage is detected, old batteries may be removed at operation 608 and new batteries installed at operation 602.

If, on the other hand, the correct battery power is detected, the workflow may proceed to set up the alarm at operation 618. Thus, the unit is in alarm setup mode. In this mode the sound level (operation 624), vibration (operation 620), and alarm tone (operation 622) sequence may be selected. The user may push the multifunction switch up at operation 624 to increase or decrease the sound level. There may be multiple sound levels. Pressing the multifunction switch up may alternate between high and low sound levels.

The user may press the multifunction switch downward at operation 628 to select vibration. Pressing the multifunction switch downward may alternate between vibration and no vibration. The user may select the desired alarm tone sequence at operation 626 by pressing the multifunction switch inward. The alarm tone sequence may step through the multiple alarm tones with each inward press. At operation 630, the alarm setup may be terminated and the workflow proceeds to decision block 632 to check whether the sensor plug is inserted into the jack. If the sensor is inserted properly the unit may beep and flash (e.g., twice). If the sensor plug is not inserted, the workflow may wait at operation 634 and then enters the low current mode at operation 636.

If the signal sensor plug is inserted but the power is insufficient, as determined at operation 640, a low voltage alarm may sound. For example, the LEDs may blink fast five times and the unit may beep fast five times. The low battery alarm may repeats after every 60 seconds and may continue until the batteries are replaced. At the same time, functionalities of the alarm unit may be impaired. If, on the other hand, the correct battery power is detected at operation 640, the workflow may proceed to the monitor mode.

In the Monitor mode the signal processing means waits for a change in state across electrodes located in the analyte sensor portion. Upon a change in state in the sensor electrodes (indicating presence of an analyte) the signal processing means enters Alarm mode and power is sent to the alarm means. The alarms means includes a vibrating means, a light emitting means, and an audible alarm means that are synchronized to vibrate, flash and sound at the same time and frequency. The user can set alarm chime type and volume or can choose not to use the audible alarm means by setting the alarm volume to zero in Alarm Setup mode. The light emitting means is always employed in the analyte detection alarm.

A snooze silent button is employable during Alarm mode with which the user can temporarily disable the power to the alarm means by quickly depressing the snooze silent button. This feature enables the user to have enough time to wake up, see what has happened, head to and use the bathroom to urinate, clean and dry the sensor and remove the sensor cable plug before the alarm means is once again enabled. The signal processing means implements a timer that is disabled if the sensor is removed during analyte detection alarm. If the sensor is not removed the timer counts until a full count is detected at which point power to the alarm means is once again enabled. The signal processing means thereby requires a multi-step alarm shut off process forcing a user to wake up to turn off the alarm but also making it easy to temporarily disable the alarm and focus on the need to urinate.

In the monitor mode, the signal processing unit may apply voltage to sensor at operation 644. The multifunction switch may have no input to the system in monitor mode. The unit monitors the sensor for moisture. The LEDs do not flash and there is no alarm sound or vibration to disturb the user. The microprocessor may go into the low current mode to reduce the current drain at operation 646. At decision block 648, the signal processing module may check whether the sensor is plugged in if the sensor is not plugged in, the workflow may proceed to operation 652 and return back to the alarm setup module. If, on the other hand, the sensor is plugged in, the workflow may proceed to decision block 650 to determine whether there is moisture on the sensor. If the sensor has moisture, the workflow may proceed to the alarm mode. Upon detection of moisture on the sensor, all power to the sensor may be removed. This prevents any electrolysis of the analyte (e.g., urine). This feature may eliminate possible irritation as the result of electrolyzed compounds. Upon detection of moisture on the sensor, the LEDs may flash fast. The alarm sound may be activated, if the unit is not in vibrating only mode. If any vibration mode has been selected the unit begins to vibrate accordingly. If the user does not press the enable button, the unit may continue to produce sound and/or vibration and the LEDs flash fast until the batteries are depleted.

The user may push the enable button and the sound and/or vibration ceases and the LEDs continue to flash fast. If the user does not remove and clean the sensor within one minute, all alarms are reinstituted. The user may remove, clean, and dry the sensor to remove the urine residue. The user may install a clean and dry sensor. If the sensor tests as clean, the unit beeps and flashes goes into the monitor mode.

The previous is a detailed description of illustrative embodiments of the present invention. As these embodiments of the present invention are described with references to the aforementioned drawings, various modifications or adaptations of the methods and or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings are not to be considered in a limiting sense, as it is understood that the present invention is in no way limited to the embodiments illustrated.

Thus, embodiments of the alarm unit for monitoring or detection of an analyte have been described. Although the embodiments have been described with reference to specific example embodiments, it will be evident that various modifications and changes may be made to these embodiments without departing from the broader spirit and scope of the system and method described herein. Accordingly, the specification and drawings are to be regarded in an illustrative rather than a restrictive sense.

The invention claimed is:

1. A system for monitoring and detection of an analyte, the system comprising:
   a signal processing unit configured to control an alarm unit in various modes of operation;
   an attachment device configured to attach the alarm unit to a clothing item of a user;
   an analyte sensor configured to be connected to the signal processing unit, the signal processing unit configured to verify the connection; and
   a power source to supply power to the alarm unit, the signal processing unit configured to determine, based on predetermined criteria, whether the power is sufficient to operate the alarm unit, wherein the connection includes an electric cable connecting the signal processing unit to the analyte sensor via an electric cable plug inserted into an electric jack of the analyte sensor.

2. The system of claim 1, wherein, based on results of the verification of the connection of the signal processing unit to the analyte sensor, the signal processing unit generates an input signal to the alarm unit to actuate the alarm unit in a predetermined combination of a sound, a vibration, and light as to indicate to the user whether the connection is active, the signal processing unit not being able to enter into a monitor mode unless the connection is active.

3. The system of claim 1, wherein the various modes include a power up mode in which the signal processing unit determines, based on predetermined parameters, whether the power source has sufficient power to operate the alarm.

4. The system of claim 1, wherein the various modes include an alarm setup mode, the alarm set up mode enabling the user to select one or more of the following: an alarm volume, an alarm tone, a vibration mode.

5. The system of claim 1, wherein the various modes include a monitor mode in which the signal processing unit detects a change in a current state across electrodes of the analyte sensor.

6. The system of claim 1, wherein the various modes include an alarm mode, the alarm mode being activated by an input signal from the signal processing unit and a signal indicating the change in the current state across the electrodes of the analyte sensor is detected.

7. The system of claim 1, wherein the alarm unit is temporarily deactivated by delaying its actuation.

8. The system of claim 1, wherein the power source includes a battery.

9. The system of claim 1, wherein the signal processing unit is encased in a protective plastic casing, the protective plastic casing being attached to clothing worn by the user with a clip.

10. The system of claim 1, wherein the signal processing unit is configured to receive an input signal from an electric jack via a plug attached to an electrical cable, the electrical cable being inserted into the electric jack and connected to the signal processing unit and capable of carrying an electric current through and from the analyte sensor.

11. The system of claim 1, where the alarm unit is configured to generate one or more of the following: an audible alarm, a vibrating alarm, a light.

12. The system of claim 1, wherein upon determining that the power is insufficient to operate the alarm unit, the signal processing unit generates an input signal to the alarm unit so as to actuate the alarm unit in a predetermined arrangement of sound, vibration and light to indicate to the user that the power source is insufficient.

13. The system of claim 1, further comprising a three-way switch configured to connect to the signal processing unit, wherein the three way switch is comprised internally of three distinct switches;
   the three way switch is attached to a plastic ridged semicircular handle portion that extends somewhat outside of the casing for easy finger manipulation;
   the three way switch only functions in an alarm setup mode whereby it is deactivated by the signal processing unit upon exiting the alarm setup mode;
   the handle portion manipulates the three switches by being pushed in the up, down, or inward direction in order to choose between and select alarm volume and chime type settings;
   the lowest volume setting results in no audible alarm volume with lights and vibrate only; and
   the three way switch is deactivated when the signal processing unit goes from Alarm Setup mode to Monitor mode after establishing that:
   the electric cable plug is inserted properly;
   that there is no analyte present on the analyte sensor;
   that the power source has sufficient power; and
   that the user has set the desired alarm settings.

14. The system of claim 1, further comprising a clip, the clip comprising a plastic body portion and a plastic perpendicular casing attachment portion comprised in part of two equally spaced apart attachment arm portions that extend downward from the plane of the casing attachment portion and include a tab portion or portions located on the inner surfaces of the downward extending attachment arm portions whereby the tab portions face each other, and wherein the clip comprises a set of parallel semicircular teeth at its bottom end that extend downward from the plastic body portion and that terminate in roughened plastic edges, and wherein a tooth bridge portion extends perpendicularly to and is attached between and to the parallel teeth so that the parallel teeth support the tooth bridge portion and whereby the bottom surfaces of the parallel teeth and the tooth bridge are aligned so as to form an elongated contact point for crimping a portion of clothing between the elongated contact point and a rubber or silicone strip portion located on the casing back, and wherein the plastic body portion top end and the bottom end occupy different horizontal planes whereby the distance between the planes is roughly equivalent to the size of the downward extension dimension of the teeth portions, and wherein the plastic body portion top end and the casing attachment portion lay flat against the back surface of the casing, and wherein the casing attachment portion acts as a fulcrum between the plastic body portion top end and bottom end during use of the clip whereby the clip teeth are lifted upwards so as to receive clothing or diaper material between the teeth and the casing back surface.

15. The system of claim 14, further comprising a casing, the casing comprising plastic, is substantially square or rectangular shaped and has rounded corners, and wherein:

the left and right side portions of the casing each contain a recessed slot portion whereby a tab portion or portions located on attachment arms of the clip may be inserted so as to enable the left and right slot portions to frictionally attach the casing to the clip; and a rubber or silicone strip portion is positioned on the casing back underneath the point of contact with a clip teeth and tooth bridge.

16. The system of claim 1, wherein the alarm unit is configured to detect whether the analyte sensor is accidently disconnected from the signal processing unit.

17. The system of claim 1, comprising an alarm delaying means wherein the alarm unit is temporarily deactivated after having been activated due to presence of an analyte on the sensor during Monitor mode and whereby the alarm delaying means comprises:

a switch with a plastic button portion that extends through the casing for external operation;

an arrangement and configuration of circuit elements that, in use, connect the switch to the signal processing unit; and activation of the switch by the user during Alarm mode generates a suitable input signal from the signal processing unit to a timer whereby:

the timer removes power to the alarm unit;

the timer may perform a full count after which power to the alarm unit is restored; and the timer may be disabled by removal of the electric cable plug from the electric jack and then reinsertion of the electric cable plug into the electric jack after the analyte has been removed from the analyte sensor portion.

\* \* \* \* \*